(12) United States Patent
Wadström et al.

(10) Patent No.: US 8,927,252 B2
(45) Date of Patent: Jan. 6, 2015

(54) SYNBIOTIC COMPOSITIONS FOR RESTORATION AND RECONSTITUTION OF GUT MICROBIOTA

(75) Inventors: Torkel Wadström, Helsingborg (SE); Asa Ljungh, Helsingborg (SE); Padma Ambalam, Rajkot (IN); Kanthi Kiran Kondepudi, Andhra Pradesh (IN)

(73) Assignee: Lavivo AB, Vastra Flolunda (SE)

( * ) Notice: Subject to any disclaimer, the term of this patent is extended or adjusted under 35 U.S.C. 154(b) by 0 days.

(21) Appl. No.: 13/983,154

(22) PCT Filed: Feb. 9, 2012

(86) PCT No.: PCT/SE2012/050131
§ 371 (c)(1),
(2), (4) Date: Sep. 5, 2013

(87) PCT Pub. No.: WO2012/108830
PCT Pub. Date: Aug. 16, 2012

(65) Prior Publication Data
US 2013/0336931 A1    Dec. 19, 2013

(30) Foreign Application Priority Data

Feb. 9, 2011 (SE) ................................. 1100084
Jun. 13, 2011 (SE) ................................. 1100455
Jun. 21, 2011 (SE) ................................. 1100487

(51) Int. Cl.
*C12N 1/22* (2006.01)

(52) U.S. Cl.
USPC ...................................... 435/252.9; 424/93.45

(58) Field of Classification Search
USPC ............................ 435/252.9; 424/93.45; 426/61
IPC ...................... A61K 35/741,35/747; C12R 1/245
See application file for complete search history.

(56) References Cited

U.S. PATENT DOCUMENTS

| 2008/0131401 A1* | 6/2008 | Brown et al. | 424/93.4 |
| 2009/0041736 A1* | 2/2009 | Sprenger et al. | 424/93.45 |
| 2010/0166721 A1* | 7/2010 | Masri | 424/93.44 |

FOREIGN PATENT DOCUMENTS

| EP | 0 856 259 A | 8/1998 |
| GB | 2 338 244 | 12/1999 |
| WO | 97/34591 | 9/1997 |
| WO | 02/060276 A | 8/2002 |
| WO | 2005077391 A | 8/2005 |
| WO | 2007/140621 | 12/2007 |

OTHER PUBLICATIONS

Ljungh A. et al., "Isolation, selection and charactheristics of *Lactobacillus paracasei* subsp. Paracasei F19", Microbial Ecology in Health and Disease, 2002, vol. 14, Supplement 3, pp. 4-6.

Kruszewska D. et al., "Selection of lactic acid bacteria as probiotic strains by in vitro tests", Microecology and therapy, 2007, vol. 29, pp. 37-49.

Timmerman et al., "Monostrain, multistrain and multispecies probiotics—A comparision of functionality and efficacy", International Journal of Food Microbiology, vol. 96, No. 3, Nov. 2004, pp. 219-233.

Wenus et al., "Prevention of antibiotic-associated diarrhoea by a fermented probiotic milk drink" European Journal of Clinical Nutrition, vol. 62, No. 2, Feb. 2008, pp. 299-301.

Chapman et al., "Health benefits of probiotics: are mixtures more effective than single strains?", European Journal of Nutrition, vol. 50, No. 1, Feb. 2011, pp. 1-17.

Williams et al., "Clinical trial: a multistrain probiotic preparation significantly reduces symptoms of irritable bowel syndrome in a double-blind placebo-controlled study", Alimentary Pharmacology & Therapeutics, vol. 29, No. 1, Jan. 2009, pp. 97-103.

International Search Report from corresponding International Application No. PCT/SE2012/050131, mailed on May 4, 2012.

International Preliminary Report on Patentability from corresponding International Application No. PCT/SE2012/050131, mailed Jan. 24, 2013.

* cited by examiner

*Primary Examiner* — Ralph Gitomer
(74) *Attorney, Agent, or Firm* — Renner, Otto, Boisselle & Sklar, LLP

(57) ABSTRACT

The present invention relates to synbiotic compositions comprising probiotic bacterial strains and prebiotic substances that, when combined exhibit synergistic behavior. The synergetic compositions will stimulate the indigenous microflora to restore and reconstitute in vivo gut like conditions after antibiotic associated diarrhea (AAD), and/or other gut infections caused by gastrointestinal pathogens, and relapses thereof, as well as the prevention of said disorders.

17 Claims, 4 Drawing Sheets

SYNBIOTIC COMPOSITIONS FOR RESTORATION AND RECONSTITUTION OF GUT MICROBIOTA

This application is a National Stage application filed under Rule 371 based upon PCT/SE2012/050131 filed Feb. 9, 2012, which claims priority to Sweden 1100084-1 filed Feb. 9, 2011, which claims priority to Sweden 1100455-3 filed Jun. 13, 2011, which claims priority to Sweden 1100487-6 filed Jun. 21, 2011.

TECHNICAL FIELD OF THE INVENTION

The present invention relates to synbiotic compositions comprising probiotic bacterial strains and prebiotic substances that, when combined exhibit synergistic behavior. The synergetic compositions will stimulate the indigenous microflora to restore and reconstitute in vivo gut like conditions after antibiotic associated diarrhea (AAD), and/or other gut infections caused by gastrointestinal pathogens, and relapses thereof, as well as the prevention of said disorders.

BACKGROUND OF THE INVENTION

The intestinal microbiota constitutes a true "extracorporeal organ" with an important role for the body's intrinsic metabolism and various immune functions. This "organ" performs unique digestive functions that simply cannot be accomplished by the gastrointestinal (GI) tract of a germ-free animal. However, together the GI and the microbiota form a complex metabolic cross talk among bacterial species and the host.

Normally the intestinal mucus layer protects the epithelium from invasion, and colonization by pathogens, and serves as a matrix in which antimicrobial factors produced by the epithelium, together with strains of the normal gut microbiota, reside. This mucus layer constitutes a buffer zone that achieves luminal compartmentalization of the microbiota and establishes a communication line for an exchange of molecules through crosstalks between bacterial strains and the intestinal epithelium (Sansonetti, Mucosal Immunol, 2011, 4:8-14).

An increasing antibiotic use in human and animal medicine, today leads to a severe amplification of antibiotic resistant strains in the gut such as methicillin resistant Staphylococci (MRSA and MRSE), extended spectrum β-lactamase producing Enterobacteriaceae (ESBL), vancomycin-resistant *Enterococcus* spp (VRE), clarithromycin-resistant *Helicobacter pylori*, vancomycin-resistant *Clostridum difficile* (CD), quinolone resistant *Campylobacter jejuni* and various strains of *Candida* species CD is in small quantities part of the indigenous normal gut flora, but broad spectrum antibiotics such as clindamycin, cephalosporins, and fluoroquinolones, which destroy the indigenous human gut microflora, will cause gut overgrowth of CD which produces toxins, killing enterocytes in the mucosa, and induce diarrhea, which in severe cases leads to pseudomembranous colitis with a high mortality. The epidemic CD strain NAP1/027 produces substantially more toxin A and toxin B than hitherto isolated hospital strains and is highly virulent.

The gut microbiota is a complex ecosystem acting in symbiosis with the host. Enteric Bifidobacteria (Bif) species possess a very high number of genes to metabolise carbohydrates in the colon whereas lactobacilli are the dominating Lactic acid bacteria (LAB) in the small intestine.

Prebiotic fermentation produces short chain fatty acids (SCFA), such as acetic acid, butyric acid and lactic acid that reduce the local pH of the colon. Moreover, prebiotics and dietary fibers help in the multiplication of LAB and bifidobacteria to yield high cell densities and prevent growth of said gut pathogens mentioned above by producing bactericidal substances, antioxidants, reducing mucosal inflammation, maintaining colonic mucosal integrity, and promoting strong host anti-inflammatory responses. Competitive exclusion is another mode of antimicrobial defense against the invading pathogens.

The current use of the probiotic and prebiotic terms are normally related to a complementary synbiotic concept, wherein the probiotic is selected based on specific beneficial effects desirable for the host, and the prebiotic is selected to stimulate the growth of indigenous microflora. However, the present invention uses the approach of a novel synergistic concept, wherein the prebiotic is selected to stimulate the growth of probiotic strains having specific beneficial effects on the host. It may also increase the levels of beneficial host GI microbiota, but the primary target is to stimulate the growth of the ingested probiotic strains. Co-culturing stimulates other partners in the composition that are poor to utilize prebiotic oligosaccharides and other non-digestible carbohydrates in the human gut.

SUMMARY OF THE INVENTION

A first aspect of the invention relates to a synbiotic composition comprising at least two bacterial strains selected from the group consisting of the *Lactobacillus* and Bifidobacteria genus, and one or more prebiotic substances, characterized in that at least one of the bacterial strains is capable of degrading starch; and at least one prebiotic substance is starch.

Advantageously the bacterial strain capable of degrading starch is of the Bifidobacteria genus, or of the *Bifidobacterium breve* species such as Bif LU 10.

Advantageously the starch is resistant starch (RS) and/or soluble starch (SS).

Advantageously one of said bacterial strains is a non-starch degrading strain, or of the *Lactobacillus paracasei* species, such as LAB LU 33.

Advantageously the synbiotic composition comprises at least Bif LU 10 and one or more of the strains LAB LU 23, LAB LU 28, LAB LU 33, BIF LU 29, and/or BIF LU 30, or at least Bif LU 10, and LAB LU 33, or at least BIF LU 10, LAB LU 33, and BIF LU 30, or at least BIF LU 10, LAB LU 33, BIF LU 30, and LAB LU 28.

Advantageously one or more of the bacterial strains has been exposed to acid, bile and/or mucin during their production, such that the exposure to acid involves lowering pH of a culture broth to pH 2-5, preferably to pH 2.5-4.5, more preferably pH to 3-4, for 15-150 min, preferably for 20-140 min, more preferably for 30-130 min, more preferably for 40-120 min during the growth of the bacterial strains, and the exposure to bile involves growing the bacterial strains in the presence of 0.1-2.5% (wt/vol), preferably 0.5-2%, more preferably 1.0-1.5% sodium taurocholate, or 1-10% (vol/vol), preferably 2-7%, more preferably 3-5% porcine bile for 2-8 hrs, preferably for 2.5-7 hrs, more preferably for 3-6 hrs, and the exposure to mucin involves growing the bacterial strains in the presence of 0.01-1% (vol/vol), preferably 0.03-0.7%, more preferably 0.05-0.5% mucin for 2-8 hrs, preferably for 2.5-7 hrs, more preferably for 3-6 hrs.

Advantageously the synbiotic composition further comprises a prebiotic substance of the group consisting of disaccharides, oligosaccharides, and/or polysaccharides, wherein the disaccharide is lactulose, the oligosaccharides are from the group consisting of fructo-oligosaccharides (FOS), galactooligosaccharides (GOS), Xylo-oligosaccharides (XOS), chitosan oligosaccharide (chioses), isomaltose oligosaccharides (IMOS), gum arabic, soy- and pectin-oligosaccharides, and the polysaccharides are from the group consisting of pectin, xylan, inulin, chitosan, and/or β-glucan.

Advantageously the synbiotic composition further comprises prebiotic substances of the group consisting of galactooligosaccharides (GOS), Xylo-oligosaccharides (XOS), isomaltose oligosaccharides (IMOS), fructo-oligosaccharides (FOS) and/or lactulose.

Advantageously the synbiotic composition further comprises galactooligosaccharides (GOS), and/or Isomaltooligosaccharides (IMOS).

The synbiotic composition as described above is advantageously used in the colonization of the intestinal mucosa of a subject, and in the prevention, treatment of, amelioration of symptoms, and/or prevention of relapse of antibiotic-associated diarrhea (AAD) and/or infections caused by gastrointestinal pathogens in a subject.

The antibiotic-associated diarrhea (AAD) is induced by *Clostridium difficile*.

The infection by gastrointestinal pathogens is caused by *Salmonella, Campylobacter jejuni*, Extended Spectrum Beta Lactamase producing (ESBL) *E. coli*.

Advantageously the subject is a mammal, such as a mammal of the group that consists of humans, nonhuman primates, cattle, sheep, pigs, goats and horses, dogs, cats, rodents and guinea pigs. Preferably the subject is a human.

The synbiotic composition as described above may be used in the manufacture of a medicament for use in the colonization of the intestinal mucosa of a subject to prevent, treat, ameliorate symptoms of, and prevent relapse of antibiotic-associated diarrhea (AAD), and/or infections caused by gastrointestinal pathogens.

The synbiotic composition as described above may be used for the manufacture of a medicament for use in the treatment of a subject suffering from antibiotic-associated diarrhea (AAD), and/or infections caused by gastrointestinal pathogens.

The synbiotic composition as described above may be used in a method for the colonization of the intestinal mucosa of a subject, said method comprising the step of administering the synbiotic composition in an effective dose to a subject in need thereof.

The synbiotic composition as described above may be used in a method for treating a subject for antibiotic-associated diarrhea (AAD) and/or infections caused by gastrointestinal pathogens, said method comprising the step of administering the synbiotic composition in an effective dose to a subject in need thereof.

DEFINITIONS

The terms used in this invention are in general expected to adhere to standard definitions accepted by those having ordinary skill in the art of microbiology and biochemistry. A few exceptions, as listed below, have been further defined within the scope of the present invention.

As used herein the term "disaccharide" is the carbohydrate formed when two mono-saccharides undergo a condensation reaction which involves the elimination of a small molecule, such as water, from the functional groups only.

As used herein the term "oligosaccharide" refers to a saccharide polymer containing a small number of sugars (monosaccharides), usually two to ten.

As used herein the term "polysaccharides" are polymeric carbohydrate structures, formed of repeating units (mono- or di-saccharides) joined together by glycosidic bonds. These structures are often linear, but may contain various degrees of branching.

As used herein the term "starch" is a carbohydrate consisting of a large number of glucose units joined together by glycosidic bonds. This polysaccharide is produced by all green plants as an energy store. It consists of two types of molecules: the linear and helical amylose and the branched amylopectin. Depending on the plant, starch generally contains 20 to 25% amylose and 75 to 80% amylopectin. The term starch includes, but is not limited to soluble starch (SS), resistant starch (RS) from the cereals (rice, wheat, and maize), the root vegetables (potatoes and cassava), acorns, arrowroot, arracacha, bananas, barley, breadfruit, buckwheat, canna, colacasia, katakuri, kudzu, malanga, millet, oats, oca, polynesian arrowroot, sago, sorghum, sweet potatoes, rye, taro, chestnuts, water chestnuts and yams, beans, such as favas, lentils, mung beans, peas, and chickpeas.

As used herein the term "probiotics" refers to bacteria which, when consumed in sufficient amounts confer a benefit to health.

As used herein the term "prebiotics" refers to substances that are non-digestible food ingredients that stimulate the growth and/or activity of bacteria in the digestive system in ways claimed to be beneficial to health.

As used herein the term "synbiotics" refers to nutritional supplements or medicament for combining probiotics and prebiotics in a form of synergism. A synbiotic composition will stimulate the growth of probiotics strains present in the composition and in the indigenous microflora and to exhibit synergistic effect in vivo.

As used herein the term "subject" refers to any living organism such as an animal or human in need of treatment for, or susceptible to, a condition involving an unwanted or undesirable microorganism, e.g. a particular treatment for having an unwanted gastrointestinal pathogen as defined below. The term subject includes, but is not limited to, humans, nonhuman primates and monkey species, farm animals such as, pigs, goats and horses, domestic mammals such as dogs and cats, laboratory animals including rodents such as mice, rats and guinea pigs. The term does not denote a particular age or sex. Thus, adults and newborn subjects, whether male or female, are intended to be covered). In preferred embodiments, the subject is a mammal, including humans and non-human mammals. In the most preferred embodiment, the subject is a human. As used herein the term "pathogenic" refers to a substance or condition that has the capability to cause a disease.

As used herein the terms "gastrointestinal pathogen" or "enteropathogen" include microbes with pathogenicity for the gastrointestinal tract (from oesophagus down to rectum). It includes *enterobacteria, enterococci, corynebacteria, Mycobacterium avium* subspecies *paratuberculosis, Brachyspira hyodysenteriae, Lawsonia intracellularis, campylobacter, clostridia*. Gastrointestinal pathogenic bacteria may include bacteria of the genus *Salmonella, Shigella, Staphylococcus, Campylobacter jejuni, Clostridium, Escherichia coli, Yersinia, Vibrio cholerae*, and others.

As used herein the terms "bacteriocins" or "bacteriocin like substances" are proteinasceous toxins produced by bacteria to inhibit the growth of similar or closely related bacterial strains. As used herein the term "treatment" includes the attempted prevention, remediation, amelioration, and the prevention of relapse of a health problem in a subject, usually following a diagnosis.

DETAILED DESCRIPTION OF THE INVENTION

Figure 1:
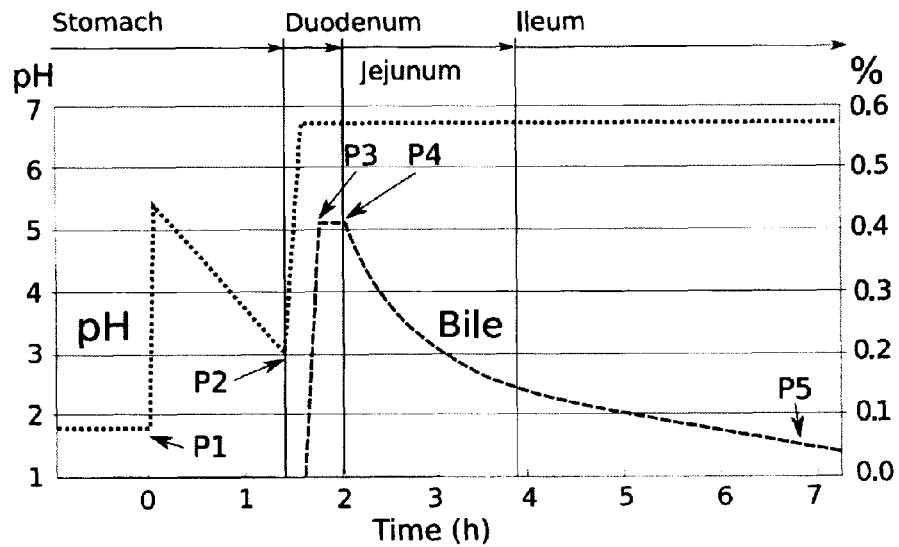
FIG. 1 Algorithm for the gastrointestinal-like transit simulator (GITS).

The present invention relates to symbiotic compositions comprising at least two probiotic strains of the Lactobacilli (LAB) and/or Bifidobacteria (Bif) genus and one or more prebiotic substances. At least one of the bacterial strains should have the capacity to degrade starch, and at least one of the prebiotic substances present in the composition should be starch. The bacterial strains should have the ability to adhere to the intestine and inhibit toxins A and B produced by *C. difficile*, but not the growth of each other. Furthermore the at least one or more prebiotic substances present in the composition should enhance growth of the probiotic strains but not that of gastrointestinal pathogens. The symbiotic compositions of the present invention are advantageously used for the colonization of the intestinal mucosa of a subject to prevent, treat, ameliorate symptoms of, and prevent relapse of antibiotic-associated diarrhea (AAD), and/or infections caused by gastrointestinal pathogens.

In the present study more than 75 different probiotic strains of the *Lactobacillus* and Bifidobacteria genus have been screened and characterized regarding beneficial properties such as adhesion to the mucus layer of the intestine, antimicrobial activities against *C. difficile* (CD) and/or other gut pathogens, degradation of prebiotic substances and the production of antioxidants etc. Surprisingly, it turned out that these properties are very strain specific and not general for all strains of a genus.

Lactobacilli belong to a group of (microaerophilic) bacteria comprising more than 100 different *Lactobacillus* species which produce lactic acid during growth. They constitute the dominant part of the normal vaginal flora and the newborn intestine but they also form part of the normal flora of adults. Lactobacilli are able to grow at low pH and tolerate >20% bile in the growth medium. The production of lactic acid makes their environment acidic, which inhibits the growth of some harmful bacteria. *L. acidophilus, L. plantarium, L. casei, L. paracasei, L. reuteri, L. rhamnosus, L. bifidus*, and *L. bulgaricus* are some important species of the *Lactobacillus* genus that may be used in the composition of the present invention.

Bifidobacteria belong to an anaerobic group of bacteria which colonize the newborn gut and gradually decreases with age. They exert beneficial effects during growth including the regulation of intestinal microbial homeostasis, the inhibition of pathogens and harmful bacteria that colonize and/or infect the gut mucosa, the modulation of local and systemic immune responses, the repression of pro-carcinogenic enzymatic activities within the microbiota, the production of vitamins, and the bioconversion of a number of dietary compounds into bioactive molecules. *B. longum, B. breve, B. animalis, B. bifidum, B. infantis* are examples of species of the *Bifidobacterium* genus that may be used in the composition of the present invention.

Following the initial screening, six strains (i.e. LAB LU28, LAB LU 33, Bif LU 10, Bif LU 29 and Bif LU 30) were eventually selected from the group of more than 75 probiotic strains based on their beneficial properties as discussed above. The selected strains were thereafter tested regarding their capability of surviving and multiplying, as well as exhibiting anti-microbial activity (AMA) during growth in the presence of each other, i.e. during co-culture. All of the selected lactobacilli and bifidobacteria strains survived co-culture well and did not produce bacteriocin like substances against each other.

The selected strains were also investigated regarding their utilization of prebiotics such as galactooligosaccharides (GOS), Xylo-oligosaccharides (XOS), isomaltose oligosaccharides (IMOS), fructo-oligosaccharides (FOS), lactulose, gum arabic, beta glucan, xylan, pectin, inulin and/or soluble and resistant starch, when co-cultured with each other. Co-culture of selected probiotic strains stimulated growth of specific bacterial strains depending on their prebiotic degrading ability in the different combinations of prebiotics. Surprisingly, co-culture of a non-starch degrading strain and a starch degrading strain, in the presence of starch as the only available prebiotic substance, stimulated growth of the non-starch degrading strain. The AMA of such compositions was retained against CD and other gut pathogens. This indicated a novel concept of cross-feeding and demonstrates the synergy exhibited between the strains of the composition of the present invention. This concept is used when developing optimal compositions to be used in the colonization of the intestinal mucosa of a subject to prevent, treat, ameliorate symptoms of and prevent relapse of antibiotic associated diarrhea (AAD), and/or infections caused by gastrointestinal pathogens.

Cell free supernatant (CFS) from Co-cultures of two or more of the selected strains with different combinations of prebiotics exhibited AMA against pathogens ESBL *E. coli, S. aureus, C. difficile* 2167 and NAP1/027. Surprisingly, AMA was retained when the CFS extract was diluted up to 1:500 against some pathogens and 1:10 against others, an activity which was significantly higher than from strains grown as mono-cultures. This clearly shows that selected strains exhibit synergism among each other leading to high AMA against pathogens. Furthermore co-culture of a mix of selected strains and CD, reduced growth of CD, and production of Toxin A and B by CD were strongly inhibited by the presence of the selected probiotic strains.

In said composition it is an advantage, but not necessarily a requirement that one or more of the bacterial strains have been exposed to acid, bile and/or mucin during the production of the bacterial strains. Acid and/or bile exposure induce stress responses in the bacteria which enhance their ability to survive transport through the gastrointestinal tract and to colonize the intestinal mucus layer where they produce antimicrobial activity (AMA) enabling the strains to exert beneficial effects.

The exposure to acid may involve lowering the pH of the culture broth wherein one or more of the bacterial strains are grown in MRS media to pH 2-5, preferably to pH 2.5-4.5, more preferably pH to 3-4, for 15-150 min, preferably for 20-140 min, more preferably for 30-130 min, more preferably for 40-120 min. The exposure to bile may involve the addition of 0.1-2.5% (wt/vol), preferably 0.5-2%, more preferably 1.0-1.5% sodium taurocholate, or 1-10% (vol/vol), preferably 2-7%, more preferably 3-10% porcine bile, a culture broth for 2-8 hrs, preferably for 2.5-7 hrs, more preferably for 3-6 hrs during the production of the bacterial strains. The exposure to mucin involves growing the bacterial strains in the presence of 0.01-1% (vol/vol), preferably 0.03-0.7%, more preferably 0.05-0.5% mucin for 2-8 hrs, preferably for 2.5-7 hrs, more preferably for 3-6 hrs during the production of the bacterial strains.

Usually bacteria are cultured in a medium which is "just" optimal for growth. Exposure to acid, bile or mucin during growth is a stress for the bacteria. As a defense, stress genes are induced which in turn induce production of Heat Shock Proteins (HSP) and other stress proteins which turn the bacteria more robust. The exposure to acid and bile stress mimics the condition of the gastrointestinal tract. The stability, robustness and synergy of compositions of selected strains with prebiotics were confirmed in a gastro-intestinal-tract simulator (GITS) model as well as in in vivo mouse models.

Based on the studies regarding co-culture, co-feeding, AMA against CD and gut pathogens, toxin inhibition activity, ability to tolerate exposure to acids, bile and/or mucin, as well as the in vitro simulations (GITS model) and in vivo mouse models, optimal components of the composition of the invention were selected. The composition of the invention comprises at least two probiotic strains of the Lactobacilli (LAB) and/or Bifidobacteria (Bif) genus and one or more prebiotic substances. Furthermore, at least one of the bacterial strains has the capacity to degrade starch, and at least one of the prebiotic substances present in the composition is starch.

Advantageously, the bacterial strain capable of degrading starch is of the Bifidobacteria genus, such as e.g. a *Bifidobac-*

*terium breve* species or more specifically the Bif LU 10 strain. The starch degrading bacterial strain of the invention is capable of degrading starch such as soluble starch (i.e. starch that can be degraded in the gut), and/or resistant starch (i.e. starch that cannot be degraded in the gut). Advantageously, the symbiotic composition of the invention further comprises a non-starch degrading strain that is of the *Lactobacillus paracasei* species such as LAB LU 33.

Thus, advantageous compositions of the present invention comprise at least Bif LU 10 and one or more of the strains LAB LU 23, LAB LU 28, LAB LU 33, BIF LU 29, and/or BIF LU 30. A further advantageous composition comprises at least Bif LU 10, and LAB LU 33, or at least BIF LU 10, LAB LU 33, and BIF LU 30. Still a further advantageous composition comprises at least BIF LU 10, LAB LU 33, BIF LU 30, and LAB LU 28. Advantages of the described compositions are disclosed below The symbiotic composition of the invention may, besides starch, comprise further prebiotic substances that are of the group consisting of disaccharides, oligosaccharides, and/or polysaccharides. The disaccharide may be lactulose. The oligosaccharides may be from the group consisting of fructo-oligosaccharides (FOS), galactooligosaccharides (GOS), Xylo-oligosaccharides (XOS), chitosan oligosaccharide (chioses), isomaltose oligosaccharides (IMOS), gum arabic, soy- and pectin-oligosaccharides. The polysaccharides may be from the group consisting of pectin, xylan, inulin, chitosan, arabinoxylan, and/or β-glucan.

Preferably at least one or more of the further prebiotic substances besides starch are of the group consisting of galactooligosaccharides (GOS), Xylo-oligosaccharides (XOS), isomaltose oligosaccharides (IMOS), fructo-oligosaccharides (FOS) and/or lactulose.

Thus, a composition of the invention may e.g. comprise two or more of the bacterial strains as described above, starch and one or more further prebiotic substance of the group consisting of galactooligosaccharides (GOS), Xylo-oligosaccharides (XOS), isomaltose oligosaccharides (IMOS), fructo-oligosaccharides (FOS) and/or lactulose.

The composition of the present invention can advantageously be used to colonize the intestinal mucosa of a subject. As used herein the term "subject" refers to any living animal or human in need of treatment for, or susceptible to, a condition involving an unwanted or undesirable gastrointestinal microorganism, eg, a particular treatment for having an unwanted pathogenic gastrointestinal infection as defined above. In preferred embodiments, the subject is a mammal, including humans and non-human mammals. Its use is particularly advantageous when the subject is a human.

In one embodiment of the invention the composition of the invention is used to prevent, treat, ameliorate symptoms of, and/or prevent relapse of *Clostridium difficile* associated diarrhea (CDAD) and/or infections caused by gastrointestinal (GI) pathogens. As used herein, the term "gastrointestinal pathogens" refers to viruses, parasites and bacteria that may cause infections in a subject, e.g. when the subject is a mammal such as a human. Gastrointestinal pathogenic bacteria may include bacteria of the genus *Salmonella, Shigella, Staphylococcus, Campylobacter jejuni, Clostridium, Escherichia coli, Yersinia, Vibrio cholerae*, and others.

Advantageously the composition may be used to prevent, treat, ameliorate symptoms of, and/or prevent relapse of antibiotic associated diarrhea (AAD) induced by strains of *Clostridium difficile* of different virulence and ribotypes. *Clostridium difficile* is an anaerobic species of the *Clostridium* genus which in low counts form part of the normal intestinal flora. *C. difficile* is the most serious cause of antibiotic-associated diarrhea (AAD) and can lead to pseudomembranous colitis, a severe infection of the colon, often resulting from eradication of the normal gut flora by antibiotics. During growth *C. difficile* produces and secretes virulence factors, e.g. Toxin A and B. Toxin A is toxic for all cells, while Toxin B is toxic for enterocytes, as it damages the cells and induces secretion (diarrhea). The composition of the invention may be used to prevent, treat, ameliorate symptoms of, and prevent relapse of antibiotic associated diarrhea (AAD) induced by strains of *Clostridium difficile* of the group consisting of ribotypes CD NAP1/027, CD 1939, CD2167, CD 1958, CD 2165, CD 2166, CD2168, CD 027 and CD 1551.

A further aspect of the invention provides a use of the composition described above, for the manufacture of a medicament for use in the colonization of the intestinal mucosa of a subject and to prevent, treat, ameliorate symptoms of, and prevent relapse of antibiotic associated diarrhea (AAD), and/or infections caused by gastrointestinal pathogens in said subject.

A further aspect of the invention provides a use of the composition described above, for the manufacture of a medicament for use in the treatment of a subject suffering from antibiotic associated diarrhea (AAD), and/or infections caused by gastrointestinal pathogens.

A further aspect of the invention provides a use of the composition described above, for the manufacture of a medicament for use in the prevention of a relapse of antibiotic associated diarrhea (AAD), and/or infections caused by gastrointestinal pathogens in a subject.

The prebiotic substances and probiotic strains of the composition in the present invention may be isolated in any level of purity by standard methods and purification can be achieved by conventional means known to those skilled in the art, such as distillation, recrystallization and chromatography.

The cultivated bacterial cells to be used in the composition are separated from the broth with any method including, without limitations, centrifuging, filtration or decantation. The cells separated from the fermentation broth are optionally washed by water, saline (0.9% NaCl) or with any suitable buffer. The wet cell mass obtained may be dried by any suitable method and preferably by lyophilisation.

The prebiotic substances and probiotic strains of the composition in the present invention may be administered alone or in combination with pharmaceutically acceptable carriers or diluents, and such administration may be carried out in single or multiple doses.

In a composition of the present invention, the prebiotic component is present in an amount comprised from 5 to 99% by weight, based on the total weight of the composition; preferably from 30% to 95%, more preferably from 50 to 90% by weight. In turn, the probiotic component is present in an amount comprised from 1 to 15% by weight, based on the total weight of the composition; preferably, from 5 to 10%. The part lacking to 100% by weight of the synbiotic composition, if any, consists of the additional substances such as adjuvants and/or excipients or proper additives/carriers.

In a pharmaceutical composition (e.g. tablets) the composition of the invention is comprised from 40 to 70% by weight, based on the total weight of the pharmaceutical composition, and the remaining part is made of pharmaceutically acceptable adjuvants and/or excipients. In a food composition (e.g. yogurt or chocolate) the synbiotic composition is comprised from 1 to 15% by weight, based on the total weight of the food composition.

In a preferred embodiment, the symbiotic composition contains bacterial strains in an amount comprised from $1 \times 10^8$ to $1 \times 10^{13}$ CFU/g, with respect to the weight of the symbiotic composition, preferably from $1 \times 10^9$ to $1 \times 10^{11}$ CFU/g.

Compositions may, for example, be in the form of tablets, pills sachets, vials, hard or soft capsules, aqueous or oily suspensions, aqueous or oily solutions, emulsions, powders, granules, syrups, elixirs, lozenges, reconstitutable powders, liquid preparations, creams, troches, hard candies, sprays, creams, salves, jellies, gels, pastes, injectable solutions, liquid aerosols, dry powder formulations, HFA aerosols or organic or inorganic acid addition salts.

The compositions of the invention may be in a form suitable for administration through oral, or by inhalation or insufflation (e.g. nasal, tracheal, bronchial) routes.

For oral, buccal or sublingual administration, the prebiotic substances and probiotic strains of the present invention may be combined with various excipients. Liquid compositions for oral administration may be in the form of, for example, emulsions, syrups, or elixirs, or may be presented as a dry product for reconstitution with water or other suitable vehicle before use. Other suitable fillers, binders, disintegrants, lubricants and additional excipients are well known to a person skilled in the art.

The invention also pertains to a composition as defined above, wherein the composition is at least one of or part of a food composition, a food supplement, a nutraceutical composition, a pharmaceutical composition and animal feed.

A further aspect of the invention provides a method for the colonization of the intestinal mucosa, and the prevention, treatment, amelioration of symptoms of, and prevention of a relapse of antibiotic associated diarrhea (AAD) and/or infections caused by gastrointestinal pathogens in a subject, said method comprising the steps of administering the composition as described above in an effective dose to the subject in need thereof. Depending upon the disorder and patient to be treated and the route of administration, the compositions may be administered at varying doses. In a preferred embodiment, the composition contains bacterial strains in an amount comprised from $1 \times 10^7$ to $1 \times 10^{13}$ CFU/dose and bacterial strain, preferably from $1 \times 10^9$ to $1 \times 10^{11}$ CFU/dose and bacterial strain.

The advantages of the present invention will now be illustrated by way of experiments. However, the described experiments mentioned below are only given as examples and should not be limiting to the present invention. Other solutions, uses, objectives, and functions within the scope of the invention as in the claims should be apparent for the person skilled in the art.

Rational for the Selection of Strains for the Composition of the Invention

The main selection criteria for the most promising strains from a strain bank used were antimicrobial activity (AMA) against gut pathogens including *Clostridium difficile*, and ability to adhere to the intestinal wall, as measured by Congo red binding (CRB) and Salt aggregation test (SAT). The next criterion was the fermentation of at least one or more than one prebiotic substance. The screening results of the tested strains are presented in Table 1.

Cell surface hydrophobicity (CSH) is an important property of a microbe to bind and interact in the intestine and compete with pathogens in the mucus layer. CSH was determined on the basis of CRB and SAT assays as follows. CRB was performed by incubating washed cells with Congo red (100 micrograms/ml in PBS) for 10 min followed by centrifugation (9,000 g×30 min). Residual Congo red in the supernatant was determined by measuring absorbance at 480 nm. Congo red in phosphate buffer saline (PBS, pH 7.2, 0.015 M) was used as control. CRB is expressed as percentage of Congo red bound. Hence the closer the result is to 100 the higher the cell surface hydrophobicity. CSH was determined by the Salt Aggregation Test (SAT) Ten microliters of washed cell suspension in PBS was mixed with 10 microliters of ammonium sulphate at pH 6.8 of various molarities ranging from 0.02 M to 4 M on a glass-slide. After one minute aggregation was observed. The results of SAT are expressed as the lowest concentration of the salt (M) at which the strain aggregates. Lower salt concentration needed for aggregation means higher cell surface hydrophobicity.

The AMA of the potential probiotic strains was determined against the gut pathogens ESBL *E. coli, S. aureus, Salmonella typhimurium* and four different strains of *C. difficile* using a microtiter plate (MTP) assay as follows: Cell free supernatant culture (CFS) filtrates were harvested from 24 h old cultures of lactobacilli and bifidobacteria grown on MRS (De Man Rogosa Sharpe) and MRSC (MRS with 0.05% (w/v) L-cysteine hydrochloride) broth by centrifugation (3,200 g, 20 min, 4° C.) and the supernatant was filter sterilized using 0.2 micrometer filter. To determine AMA, the CFS was added to a MTP. Different dilutions (1:1, 1:10, 1:100 and 1:500) were prepared in sterilised brain heart infusion (BHI) broth. 100 microliters of the supernatant, was added to microtiter wells and incubated at 37° C. overnight anaerobically using an Anoxomat® culture system (MART, The Netherlands) to equilibrate. Gut pathogen cells were grown on Fructose Fastidious agar plates for 24 h anaerobically. The cells were washed twice PBS, and re-suspended in sterile PBS. Ten microliters of gut) pathogen cells with $A_{620}=0.02$ was prepared in BHI broth and added to the overnight pre-reduced MTP. Growth was measured after 48 h (CD pathogens)/24 h (other pathogens) at $OD_{620}$ using a plate reader and result was expressed as percent inhibition of gut pathogen growth calculated relative to growth in control well without CFS.

$$\% \text{ Inhibition of } CD \text{ growth} = 100 - \left(\frac{ODt \times 100}{ODc}\right)$$

ODt and ODc represent growth of CD in the presence and absence of CFS of LAB or bifidobacteria. Similarly, AMA of co-cultured extract of lactobacilli and bifidobacteria was determined against CD. The same formula was used for all the gut pathogens.

A preliminary screening of the ability of potential probiotic strains to degrade prebiotics was performed as follows: Lactobacilli and Bifidobacteria strains were initially grown on MRS/MRSC agar under micro-aerophilic and anaerobic condition at 37° C. A single colony of each strain was then spread as a small patch on basal MRS agar without glucose and with 1% (wt/vol) prebiotic (Frutooligosaccharides (FOS), Xylooligosacharides (XOS), galactooligosaccharides (GOS), Inulin, soluble starch (SS), resistant starch (RS), pectin, isomaltooligosaccharides (IMOS), Lactulose) for Lactobacilli or proteose peptone yeast extract (PY) agar supplemented with 0.05% (w/v) L-cysteine hydrochloride agar for bifidobacteria with 1% (wt/vol) prebiotic (FOS, FOS (Orafti), XOS, GOS, Inulin, SS, RS, pectin, IMOS, Lactulose) as the major carbon source, and 30 mg of bromocresol purple per liter and was incubated under microaerophilic (for lactobacilli) or anaerobic condition (for bifidobacteria) at 37° C. for 48 h. The degradation ability of FOS, FOS (Orafti), XOS, GOS, inulin, SS, RS and pectin by various LAB and bifidobacteria can be seen in Table 1 (see footnote).

TABLE 1

Screening results for Congo Red binding, salt aggregation test, AMA and degradation of prebiotics.

| No | Strain | Congo Red binding | | Salt aggregation | | Antimicrobial activity | | | | | | | | | | | | | | | | | | | Degradation of prebiotics | | | | | | |
|---|---|---|---|---|---|---|---|---|---|---|---|---|---|---|---|---|---|---|---|---|---|---|---|---|---|---|---|---|---|---|---|
| | | Agar | Broth | Agar | Broth | CD 1939 1:1 | 1:10 | CD 2167 1:1 | 1:10 | CD 1958 1:1 | 1:10 | CD 2165 1:1 | 1:10 | CD 2166 1:1 | 1:10 | CD 2168 1:1 | 1:10 | CD 027 1:1 | 1:10 | CD 1551 1:1 | 1:10 | FOS | oraf | XOS | GOS | Inu | SS | RS | Pec |
| 1 | LAB IU 01 | 69 ± 0.3 | 41.6 ± 1.6 | ≤0.02 | ≤0.02 | L | M | L | H | M | H | H | H | H | M | H | M | H | M | nd | nd | 2+ | − | − | − | − | − | − | − |
| 2 | LAB IU 02 | 68 ± 1.7 | 48.5 ± 0.87 | ≤0.02 | ≤0.02 | M | H | M | H | M | H | H | M | H | M | H | M | H | M | nd | nd | 2+ | − | − | + | − | − | − | − |
| 3 | LAB IU 03 | 72 ± 0.5 | 44.7 ± 1.84 | ≤0.02 | ≤0.02 | L | M | L | M | M | H | H | M | H | M | H | M | H | M | nd | nd | 2+ | Nd | Nd | Nd | − | − | − | − |
| 4 | LAB IU 04 | nd | 18.2 ± 0.75 | ≥3.2 | ≥3.2 | M | H | L | L | H | H | H | M | H | M | H | M | H | M | nd | nd | 2+ | − | − | − | − | − | − | − |
| 5 | LAB IU 05 | 14 ± 4 | 19.6 ± 4.9 | ≤0.02 | ≤0.02 | M | H | M | L | H | H | H | M | H | L | H | L | M | M | nd | nd | 2+ | − | − | Nd | − | − | − | − |
| 6 | LAB IU 06 | 20 ± 1.1 | 19.5 ± 0.38 | ≥3.2 | ≥3.2 | M | H | M | H | M | M | H | M | H | L | H | L | M | M | nd | nd | 2+ | Nd | Nd | Nd | − | − | − | − |
| 7 | LAB IU 07 | 51 ± 1.1 | 28.1 ± 0.5 | ≤0.02 | ≤0.02 | M | H | M | H | M | H | H | L | H | M | H | L | H | M | nd | nd | V+ | − | − | − | − | − | − | − |
| 8 | LAB IU 08 | 13 ± 1.7 | 21.5 ± 1.37 | ≥3.2 | ≥3.2 | M | H | M | H | L | H | H | M | H | L | H | L | H | H | nd | nd | 2+ | − | − | Nd | − | − | − | − |
| 9 | LAB IU 09 | 75± | 10 | ≤0.02 | ≤0.02 | H | H | L | H | H | H | H | M | H | M | M | L | M | M | nd | nd | − | Nd | Nd | 3+ | − | − | − | − |
| 10 | LAB IU 10 | 36.8 ± 0.67 | 1.8 | ≥1.6 | ≥1.6 | M | H | M | M | M | M | H | N | H | M | L | L | H | H | nd | nd | 2+ | − | − | 3+ | − | − | − | − |
| 11 | LAB IU 11 | 21 ± 5 | 19.4 ± 1.5 | ≥3.2 | ≥3.2 | M | L | M | L | M | L | M | L | M | L | L | L | H | M | nd | nd | W+ | Nd | Nd | Nd | − | − | − | − |
| 12 | LAB IU 12 | 7.7 ± 1.6 | 27.7 ± 4.4 | ≥4 | ≥4 | H | H | L | H | L | L | L | M | H | M | H | M | L | L | M | M | − | − | − | W+ | − | − | − | − |
| 13 | LAB IU 13 | 6.3 ± 3 | 18.7 ± 0.31 | ≥3.2 | ≥3.2 | M | L | M | H | M | L | H | L | H | L | H | L | M | L | H | H | 2+ | Nd | Nd | Nd | − | − | − | − |
| 14 | LAB IU 14 | 11 ± 1 | 18 ± 1 | ≥3.2 | ≥3.2 | M | M | L | H | H | H | H | M | H | M | H | L | H | L | H | M | − | − | − | Nd | − | − | − | − |
| 15 | LAB IU 15 | 27 ± 1.81 | 13 ± 4 | ≥3.2 | ≥3.2 | M | H | M | M | H | H | H | L | H | L | H | M | H | L | H | L | − | Nd | Nd | Nd | − | − | − | − |
| 16 | LAB IU 16 | 24 ± 4 | 7 ± 4 | ≤0.02 | ≤0.02 | H | L | M | H | H | H | H | L | H | L | H | L | M | L | H | L | Nd | Nd | Nd | Nd | − | − | − | − |
| 17 | LAB IU 17 | 37 ± 6 | 12 ± 1 | ≥3.2 | ≥3.2 | H | M | M | L | L | nd | M | M | H | L | M | L | M | M | L | L | 2+ | − | − | − | − | − | − | − |
| 18 | LAB IU 18 | 26 ± 11 | 10 ± 4 | ≥3.2 | ≥3.2 | M | L | M | M | nd | nd | M | L | nd | nd | H | M | M | L | H | M | − | Nd | Nd | Nd | − | − | − | − |
| 19 | LAB IU 19 | 6.6 ± 2 | 6 ± 0.9 | ≥4 | ≥4 | M | L | M | M | nd | nd | H | L | M | L | M | L | M | L | M | L | 2+ | − | − | − | − | − | − | − |
| 20 | LAB IU 20 | 13 ± 6 | nd | ≥3.2 | ≥3.2 | M | M | H | M | nd | nd | H | L | nd | nd | M | L | M | L | M | L | 0 | 0 | 0 | 0 | − | − | − | − |
| 21 | LAB IU 21 | nd | 6 ± 2 | nd | ≥4 | 0 | L | M | L | nd | nd | H | L | nd | nd | M | L | M | L | H | M | − | − | − | 3+ | − | − | − | − |
| 22 | LAB IU 22 | 28 ± 3.4 | 21 ± 1.7 | ≥3.2 | ≥3.2 | 0 | 0 | M | M | nd | nd | M | L | nd | nd | nd | nd | M | L | H | L | 2+ | Nd | Nd | Nd | − | − | − | − |
| 23 | LAB IU 23 | nd | 30 ± 4 | nd | ≥4 | 0 | 0 | M | H | nd | nd | M | M | nd | nd | M | L | M | M | M | M | − | − | − | − | − | − | − | − |
| 24 | LAB IU 24 | 12 ± 1.5 | 7 ± 2 | ≤0.02 | ≤0.02 | M | 0 | M | L | nd | nd | H | M | nd | nd | M | L | M | L | M | M | − | Nd | Nd | Nd | − | − | − | − |
| 25 | LAB IU 25 | 25 ± 3 | 26 ± 3 | ≤0.02 | ≤0.02 | 0 | 0 | M | H | nd | nd | H | L | nd | nd | nd | nd | M | M | H | H | − | − | − | − | − | − | − | − |
| 26 | LAB IU 26 | 37 ± 2 | 21 ± 2 | ≥3.2 | ≥3.2 | 0 | L | M | M | nd | nd | H | L | nd | nd | M | M | H | L | M | L | Nd | Nd | Nd | Nd | − | − | − | − |
| 27 | LAB IU 27 | nd | 31 ± 2 | 0 | ≤0.02 | M | M | L | L | nd | nd | M | L | nd | nd | M | L | L | L | L | L | 0 | 0 | 0 | 0 | − | − | − | − |
| 28 | LAB IU 28 | 84 ± 2 | 17 ± 1.6 | ≥3.2 | ≥3.2 | 0 | L | M | M | nd | nd | H | L | nd | nd | M | L | M | L | M | M | 2+ | − | − | 3+ | − | − | − | − |
| 29 | LAB IU 29 | 28 ± 2 | 29 ± 2 | ≤0.02 | ≤0.02 | 0 | 0 | M | H | nd | nd | H | M | nd | nd | H | L | M | L | H | H | − | Nd | Nd | Nd | − | − | − | − |
| 30 | LAB IU 30 | 21 ± 0.9 | 1 ± 4 | ≥3.2 | nd | 0 | L | M | M | nd | nd | M | L | nd | nd | M | L | M | L | H | L | − | Nd | Nd | Nd | − | − | − | − |
| 31 | LAB IU 31 | 22 ± 3 | 22.6 ± 3 | ≥3.2 | ≥3.2 | 0 | 0 | M | H | nd | nd | H | L | nd | nd | M | L | H | H | M | N | − | Nd | Nd | Nd | − | − | − | − |
| 32 | LAB IU 32 | nd | 29 ± 2 | nd | ≥4 | 0 | L | L | M | nd | nd | M | H | nd | nd | M | L | H | L | M | L | − | Nd | Nd | Nd | − | − | − | − |
| 33 | LAB IU 33 | 86 ± 1 | 22 ± 11 | ≥3.2 | ≥3.2 | 0 | 0 | M | H | nd | nd | H | H | nd | nd | H | L | M | L | M | N | 2+ | − | − | − | − | − | − | − |
| 34 | LAB IU 34 | 33 ± 1.1 | 10 ± 4 | ≥3.2 | ≥3.2 | 0 | L | M | H | nd | nd | M | L | nd | nd | M | L | M | L | H | L | − | Nd | Nd | Nd | − | − | − | − |
| 35 | LAB IU 35 | nd | 24 ± 1.75 | nd | ≥3.2 | 0 | L | M | M | nd | nd | H | H | nd | nd | H | M | H | L | H | L | W+ | Nd | Nd | Nd | − | − | − | − |
| 36 | LAB IU 36 | 44 ± 1.2 | 39 ± 4 | ≥3.2 | ≥3.2 | M | 0 | M | M | nd | nd | H | L | nd | nd | nd | nd | H | L | nd | nd | − | − | − | − | − | − | − | − |
| 37 | LAB IU 37 | 15.5 ± 1.7 | 13.5 ± 1.5 | ≤0.02 | ≤0.02 | 0 | 0 | M | H | nd | nd | H | L | nd | nd | M | M | M | N | M | M | − | − | − | − | − | − | − | − |
| 38 | LAB IU 38 | nd | 15 ± 0.8 | nd | ≥3.2 | 0 | 0 | M | N | nd | nd | M | L | nd | nd | M | M | M | L | M | L | − | Nd | Nd | Nd | − | − | − | − |
| 39 | LAB IU 39 | 16 ± 1 | 11.8 ± 1.9 | ≥3.2 | ≥3.2 | 0 | L | M | H | nd | nd | H | L | nd | nd | M | L | H | M | M | H | − | Nd | Nd | Nd | − | − | − | − |
| 40 | LAB IU 40 | nd | 29.7 ± 5 | nd | ≥3.2 | 0 | 0 | L | H | nd | nd | M | L | nd | nd | M | M | H | L | M | M | − | Nd | Nd | Nd | − | − | − | − |
| 41 | LAB IU 41 | 14.1 ± 4.8 | 2 ± 3 | ≥3.2 | ≤0.02 | 0 | 0 | M | H | nd | nd | H | M | nd | nd | M | M | M | M | H | H | − | Nd | Nd | Nd | − | − | − | − |
| 42 | LAB IU 42 | nd | 31 ± 2 | 0 | 0 | 0 | 0 | L | L | nd | nd | H | L | nd | nd | nd | nd | M | L | L | L | − | Nd | Nd | Nd | − | − | − | − |

TABLE 1-continued

Screening results for Congo Red binding, salt aggregation test, AMA and degradation of prebiotics.

| | | Congo Red binding | | Salt agregation | | Antimicrobial activity | | | | | | | | | | | | | | | | | Degradation of prebiotics | | | | | | |
|---|---|---|---|---|---|---|---|---|---|---|---|---|---|---|---|---|---|---|---|---|---|---|---|---|---|---|---|---|---|
| | | | | | | CD 1939 | | CD 2167 | | CD 1958 | | CD 2165 | | CD 2166 | | CD 2168 | | CD 027 | | CD 1551 | | | | | | | | | |
| No | Strain | Agar | Broth | Agar | Broth | 1:1 | 1:10 | 1:1 | 1:10 | 1:1 | 1:10 | 1:1 | 1:10 | 1:1 | 1:10 | 1:1 | 1:10 | 1:1 | 1:10 | 1:1 | 1:10 | FOS | oraf | XOS | GOS | Inu | SS | RS | Pec |
| 43 | LAB LU 43 | nd | 24.1 ± 3 | nd | ≥3.2 | 0 | 0 | M | L | nd | nd | M | M | nd | nd | nd | nd | M | L | M | N | − | Nd | Nd | Nd | − | − | − | − |
| 44 | LAB LU 44 | nd | 6.4 ± 2.6 | nd | ≥3.2 | 0 | 0 | M | H | nd | nd | M | H | nd | nd | nd | nd | M | H | M | L | − | − | − | 3+ | − | − | − | − |
| 45 | LAB LU 45 | 7 ± 1.1 | 2.9 ± 2 | ≥3.2 | ≥3.2 | 0 | 0 | M | H | nd | nd | H | M | nd | nd | nd | nd | M | L | H | L | 2+ | Nd | Nd | Nd | W+ | − | − | − |
| 46 | BifLU 01 | 39 ± 4 | 38 ± 3.3 | ≤3.2 | ≥3.2 | M | H | M | M | H | M | M | L | M | L | H | M | nd | nd | nd | nd | 2+ | 2+ | 2+ | 3+ | Nd | 2+ | 2+ | − |
| 47 | BifLU 02 | 17.4 ± 1.8 | 17 ± 0.2 | ≤3.2 | ≥3.2 | M | H | M | H | M | M | L | M | M | L | M | M | nd | nd | nd | nd | − | − | 2+ | 2+ | − | 0 | 0 | 0 |
| 48 | BifLU 03 | 25.6 ± 6.7 | 33 ± 0.3 | ≤0.02 | ≤0.02 | M | M | M | M | H | M | M | M | H | M | H | L | nd | nd | nd | nd | W+ | Nd | W+ | Nd | W+ | − | − | − |
| 49 | BifLU 04 | 24.2 ± 2.7 | 38 ± 3 | ≤0.02 | ≤0.02 | M | H | M | M | H | M | M | L | M | M | M | M | nd | nd | nd | nd | 2+ | 2+ | 2+ | 3+ | Nd | − | − | − |
| 50 | BifLU 05 | 34.28 ± 9 | 26 ± 7.6 | ≥3.2 | ≥3.2 | M | L | M | L | M | M | H | M | M | M | H | L | nd | nd | nd | nd | W+ | W+ | W+ | W+ | 0 | − | − | − |
| 51 | BifLU 06 | 16.1 ± 2.1 | 28 ± 2.5 | ≥3.2 | ≥3.2 | 0 | 0 | M | L | H | M | H | L | nd | nd | H | M | nd | nd | nd | nd | 2+ | Nd | Nd | Nd | W+ | − | − | − |
| 52 | BifLU 07 | 24.23 ± 1.1 | 44 ± 0.8 | ≥3.2 | ≥3.2 | L | M | L | L | H | M | M | M | nd | nd | M | L | nd | nd | nd | nd | 2+ | − | 2+ | 2+ | W+ | − | − | − |
| 53 | BifLU 08 | 37.8 ± 5.6 | 27 ± 2 | ≤0.02 | ≤0.02 | 0 | L | M | L | M | H | H | L | M | M | H | L | nd | nd | nd | nd | 2+ | Nd | + | 2+ | − | − | − | − |
| 54 | BifLU 09 | 25 ± 4 | 30 ± 4 | ≥3.2 | ≥3.2 | L | M | M | L | M | M | H | L | nd | nd | M | L | nd | nd | nd | nd | − | + | + | + | − | − | − | − |
| 55 | BifLU 10 | 22.3 ± 4.6 | 27 ± 2 | ≤0.02 | ≤0.02 | M | M | M | M | H | M | M | L | nd | nd | M | L | nd | nd | nd | nd | − | 3+ | 2+ | 3+ | W+ | 2+ | 2+ | − |
| 56 | BifLU 11 | 13 ± 8 | 21 ± 3.3 | ≥3.2 | ≥3.2 | 0 | 0 | M | L | nd | nd | L | L | nd | nd | M | L | nd | nd | nd | nd | + | Nd | Nd | Nd | − | − | − | − |
| 57 | BifLU 12 | 26 ± 6 | 33 ± 3 | ≥3.2 | ≥3.2 | 0 | 0 | M | M | H | H | M | N | nd | nd | H | L | nd | nd | nd | nd | 2+ | Nd | Nd | Nd | W+ | − | − | − |
| 58 | BifLU 13 | 20 ± 1.8 | 28 ± 3 | ≥3.2 | ≥3.2 | 0 | 0 | H | M | nd | nd | M | L | nd | nd | H | L | nd | nd | nd | nd | 2+ | Nd | Nd | Nd | − | − | − | − |
| 59 | BifLU 14 | 19.7 ± 1.7 | 28.4 ± 3 | ≤0.02 | ≤0.02 | 0 | 0 | M | L | nd | nd | L | L | nd | nd | M | L | nd | nd | nd | nd | 2+ | Nd | Nd | Nd | W+ | − | − | − |
| 60 | BifLU 15 | 21 ± 4 | nd | ≥3.2 | ≥3.2 | 0 | 0 | M | L | nd | nd | M | L | nd | nd | M | L | nd | nd | nd | nd | − | Nd | Nd | Nd | − | − | − | − |
| 61 | BifLU 16 | 15 ± 3 | 12.2 ± 2 | ≥3.2 | ≥3.2 | 0 | 0 | M | 0 | nd | nd | L | L | nd | nd | M | 0 | nd | nd | nd | nd | + | + | + | 2+ | + | − | − | − |
| 62 | BifLU 17 | 16 ± 3 | 18.2 ± 7.5 | ≤0.02 | ≤0.02 | 0 | 0 | M | N | nd | nd | M | N | nd | nd | H | 0 | nd | nd | nd | nd | + | Nd | Nd | Nd | − | − | − | − |
| 63 | BifLU 18 | 12 ± 1 | 9.5 ± 7.6 | ≥3.2 | ≥3.2 | 0 | 0 | M | N | nd | nd | M | o | nd | nd | M | N | nd | nd | nd | nd | + | 2+ | W+ | 2+ | − | − | − | − |
| 64 | BifLU 19 | 12 ± 0.9 | 10 ± 5 | ≤0.02 | ≤0.02 | 0 | 0 | M | o | nd | nd | L | L | nd | nd | M | 0 | nd | nd | nd | nd | + | 2+ | 2+ | 2+ | − | − | − | − |
| 65 | BifLU 20 | 15 ± 4 | 6.5 ± 3 | ≥3.2 | ≥3.2 | 0 | 0 | M | o | nd | nd | M | L | nd | nd | M | N | nd | nd | nd | nd | 2+ | 2+ | W+ | 3+ | W+ | − | − | − |
| 66 | BifLU 21 | 13 ± 1 | 15.5 ± 1.3 | ≤0.02 | ≤0.02 | 0 | 0 | M | L | nd | nd | H | M | nd | nd | M | 0 | nd | nd | nd | nd | 2+ | 2+ | + | 2+ | W+ | − | − | − |
| 67 | BifLU 22 | 9 ± 2.5 | nd | ≥3.2 | ≥3.2 | 0 | 0 | M | M | nd | nd | M | H | nd | nd | M | O | nd | nd | nd | nd | + | 2+ | 2+ | 2+ | + | − | − | − |
| 68 | BifLU 23 | 17.29 ± 6 | nd | ≤0.02 | ≤0.02 | 0 | 0 | M | 0 | nd | nd | L | L | nd | nd | M | L | nd | nd | nd | nd | 2+ | 2+ | 2+ | 3+ | − | − | − | − |
| 69 | BifLU 24 | 27 ± 3 | nd | ≥1.6 | ≤0.02 | 0 | 0 | M | O | nd | nd | M | 0 | nd | nd | L | O | nd | nd | nd | nd | 3+ | 3+ | 3+ | 3+ | − | 3+ | 2+ | − |
| 70 | BifLU 25 | nd | nd | ≥3.2 | ≥3.2 | 0 | 0 | M | H | nd | nd | M | H | nd | nd | M | L | nd | nd | nd | nd | − | − | − | 2+ | − | − | − | − |
| 71 | BifLU 26 | 15 ± 2 | 20 ± 2 | ≥3.2 | ≥3.2 | 0 | 0 | M | 0 | nd | nd | M | L | nd | nd | H | 0 | nd | nd | nd | nd | + | 2+ | 2+ | 2+ | − | − | − | − |
| 72 | BifLU 27 | 12 ± 2 | 12.6 ± 2 | ≥3.2 | ≥3.2 | 0 | 0 | M | H | nd | nd | M | L | nd | nd | H | O | nd | nd | nd | nd | 2+ | 2+ | 2+ | 2+ | − | − | − | − |
| 73 | BifLU 29 | 32.17 ± 0.7 | nd | ≤0.02 | ≤0.02 | 0 | 0 | M | H | nd | nd | M | O | nd | nd | H | O | nd | nd | nd | nd | − | 2+ | 2+ | 2+ | − | − | − | − |
| 74 | BifLU 30 | 22 ± 1.7 | 12.6 ± 2 | 3.2 | 3.2 | 0 | 0 | H | M | nd | nd | H | H | nd | nd | H | H | nd | nd | nd | nd | Vw+ | 3+ | 3+ | 3+ | − | − | − | − |
| 75 | BifLU 31 | 26 ± 0.73 | 31.7 ± 2.5 | 3.2 | 3.2 | 0 | 0 | H | M | nd | nd | H | L | nd | nd | H | O | nd | nd | nd | nd | Vw+ | 3+ | 3+ | 3+ | − | − | − | − |
| 76 | BifLU 32 | 13.5 ± 0.19 | 5 ± 1.16 | 3.2 | 3.2 | 0 | 0 | H | L | nd | nd | H | H | nd | nd | H | O | nd | nd | nd | nd | Vw+ | 3+ | 3+ | 3+ | − | − | − | − |

Abbreviations are as follows:
H—High activity - ≥70% inhibition,
Moderate- 41-69% inhibition,
Low ≤40% inhibition,
nd—not determined;
Vw+—very weak;
2+ strongly positive;
3+ very strongly positive.
Based on the results from the experiments presented in Table 1, probiotic strains presented in Table 2 were selected for further experiments.

Based on the results from the experiments presented in Table 1, probiotic strains presented in Table 2 were selected for further experiments. Table 2. Selected list of probiotic candidates.

| Strain | Criteria for selection |
|---|---|
| LAB LU 33 (L. paracasei F8) LMG P-26118 | LAB LU 33 was selected based on high AMA against C. difficile, ESBL E. coli, S. aureus and S. typhimurium, expression of CSH, and utilization of IMOS and lactulose. |
| LAB LU 28 (L. plantarum F44) LMG P-26120 | LAB LU 28 was selected based on very high AMA against C. difficile, ESBL E. coli, S. aureus and S. typhimurium, expression of moderate/high CSH, and significant utilization of GOS, lactulose and IMOS |
| LAB LU 23 (L. plantarum F17) LMG-P-26119 | LAB LU 23 was selected based on very high AMA against C. difficile, ESBL E. coli, S. aureus and S. typhimurium, expression of moderate/high CSH and significant utilization of GOS, lactulose and IMOS |
| Bif LU 10 (B. breve Bif 46) LMG P-26117 | Bif LU 10 showed very high AMA against C. difficile, ESBL E. coli, S. aureus and S. typhimurium, expresses high CSH and utilizes GOS and FOS to a high extent, and RS (wheat), SS. |
| Bif LU 30 (B. lactis Bif 8:8) LMG P-26116 | Bif LU 30 has very high AMA against C. difficile, ESBL E. coli, S. aureus and S. typhimurium, expresses low CSH and utilizes GOS to a greater extent followed by XOS and FOS |
| Bif LU 29 (B. longum Bif 6:18) LMG P-26115 | Bif LU 29 has very good activity against C. difficile, ESBL E. coli, S. aureus and S. typhimurium expresses high CSH, and utilizes XOS, GOS to a greater extent followed by FOS. |

The selected probiotic strains were deposited on Nov. 24, 2010 with the Belgian Coordinated Collections of Microorganisms (BCCM), Laboratorium voor Microbiologie Bacteriënverzameling (LMG), Universiteit Gent, K. L. Ledeganckstraat 35, 9000 Gent, Belgium (Web site: http://bccm.belspo.be) with the following Strain deposit nos: LAB LU 33: LMG P-26118, LAB LU 28: LMG P-26120, BIF LU 10: LMG P-26117, BIF LU 30: LMG P-26116, BIF LU 29: LMG P-26115, LAB LU 23: LMG-P-26119

Co-culture of Probiotic Strains

Different combinations of the selected bifidobacteria and LAB strains (Table 2) were tested to determine a possible synergy and compatibility of these strains with each other. To determine if bacteriocin like substances are produced by a specific strain, AMA of neutralized extracts from each strain was determined against other strains using the MTP assay. AMA extracts were obtained as in the experimental procedure described as above.

CFS obtained as in the experimental procedure described above were neutralised to pH 7 using 5N NaOH. AMA of neutralised CFS of selected bifidobacteria and lactobacilli was determined against each other using a MTP assay. Neutralized extracts of selected strains of lactobacilli or bifidobacteria used in the study did not exhibit AMA against each other (either lactobacilli or bifidobacteria). Furthermore, they did not inhibit other lactobacilli and bifidobacteria that were used as reference strains, indicating that the selected lactobacilli and bifidobacteria strains do not produce bacteriocin like substances against each other. This property of the strains was useful in developing suitable strain mixes in a "synbiotic formulation" to prevent and treat infection caused by gut pathogens and C. difficile.

Many gastrointestinal infections are caused by Salmonella, Campylobacter jejuni, and ESBL E. coli, while AAD is mainly caused by CD and MRSA. Therefore, after confirming that the selected LAB and bifidobacteria strains from Table 2 do not inhibit each other, they were co-cultured in MRSC broth and their potential AMA against CD including hypervirulent CD 027/NAP1, ESBL E. coli, S. aureus, and Salmonella typhimurium was determined using a MTP 0.5 assay.

Activated culture of the selected LAB and bifidobacteria strains from Table 2 were co-cultured by inoculating 10% inoculum of strain (total of all strains) of different LAB and/or bifidobacteria in 5 ml pre-reduced MRSC broth and allowed to grow under anaerobic conditions using an anoxomate jar at 37° C. for 24 h. After 24 h, cultures were harvested by centrifugation and the supernatant was filter-sterilized using 0.22 micrometer filter. The CFS was used to determine AMA against CD and other pathogens using MPT assay as described above or earlier. Growth was measured after 48 h (CD pathogens)/24 h (other pathogens) at $OD_{620}$ using a plate reader and the result was expressed as percent inhibition of pathogen growth calculated relative to growth in control well without CFS.

Co-cultures of different combinations of LAB LU 28, LAB LU 33, Bif LU 10 and Bif LU 30 showed high AMA against Salmonella typhimurim, E. coli, C. difficile CD NAP1/027 and S. aureus. Surprisingly, AMA was retained when the CFS extract was diluted up to 1:500 against pathogens (CD 027 and S. aureus) and 1:10 against S. typhimurim and ESBL E. coli, which was not found when strains were tested as monocultures (Table 3 & Table 4). The composition containing LAB LU 28, LAB LU 33, Bif LU 10 and Bif LU 30 showed higher AMA at 1:10 dilution against Sal. typhimurim and ESBL E. coli than was found with other combinations (Table 4). This clearly shows that selected strains exhibit synergism among the strains leading to high AMA against pathogens.

TABLE 3

AMA of different co-culture combinations containing probiotic strain against C. difficile NAP1/027, C. difficile 2167 and MRSA S. aureus

| Co-culture combination | C. difficile NAP1/027 | C. difficile 2167 | S. aureus |
|---|---|---|---|
| LAB LU 33 + Bit LU 10 (1:100) | 46 ± 0.6 | 24 ± 3 | 21 ± 12 |
| LAB LU 33 + Bif LU 10 (1:500) | 42 ± 5 | 16 ± 8 | 27 ± 7 |
| LAB LU 23 + Bif LU 10 (1:100) | 52 ± 2 | 15 ± 2 | — |
| LAB LU 23 + Bif LU 10 (1:500) | 51 ± 6 | 18 ± 3 | — |
| LAB LU 23 + LAB LU 33 + Bif LU 30 (1:100) | 36.1 ± 13 | — | 7 ± 21 |
| LAB LU 23 + LAB LU 33 + Bif LU 30 (1:500) | 11 ± 6 | — | 10 ± 14 |
| LAB LU 28 + LAB LU 33 + Bif LU 30 (1:100) | 42 ± 1 | 10 ± 1 | 30 ± 2 |
| LAB LU 28 + LAB LU 33 + Bif LU 30 (1:500) | 43 ± 1 | 5 ± 1 | 32 ± 2 |
| LAB LU 28 + LAB LU 33 + Bif LU 10 + Bif LU 33 (1:100) | 43 ± 1 | 11 ± 6 | nd |
| LAB LU 28 + LAB LU 33 + Bif LU 10 + Bif LU 33 (1:500) | 32 ± 11 | 19 ± 2 | nd |

— No inhibition, nd Not determined, CFS is obtained from MRSC containing 2% glucose and grown anaerobically

TABLE 4

AMA of different co-culture combinations containing probiotic strains against Salmonella typhimurium and E. coli

| Coculture combintaion | Salmonella typhimurium | ESBL E. coli |
|---|---|---|
| LAB LU 28 + Bif LU 10 (1:1) | 80 ± 2 | 80 ± 1 |
| LAB LU 28 + Bif LU 10 (1:10) | — | — |
| Bif LU10 + Bif LU 30 (1:10) | 81 ± 3 | 81 ± 3 |
| Bif LU 10 + Bif LU 30 (1; 100) | — | 8 ± 6 |
| LAB LU 28 + LAB LU 33 + Bif LU 30 (1:1) | 82 ± 1 | 81 ± 1 |
| LAB LU 28 + LAB LU 33 + Bif LU 30 (1:10) | — | 44 ± 12 |
| LAB LU 28 + LAB LU 33 + Bif LU 10 + Bif LU 33 (1:1) | 85 ± 1 | 86 ± 3 |

TABLE 4-continued

AMA of different co-culture combinations containing probiotic strains against *Salmonella typhimurium* and *E. coli*

| Coculture combintaion | Salmonella typhimurium | ESBL *E. coli* |
|---|---|---|
| LAB LU 28 + LAB LU 33 + Bif LU 10 + Bif LU 33 (1:10) | 89 ± 1 | 62 ± 5 |

— No inhibition, nd Not determined, CFS is obtained from MRSC containing 2% glucose and grown anaerobically Moreover, AMA produced by the selected strains against *C. difficile* correlated well to the reduced amount of toxin produced by hypervirulent strain CD NAP1/027. No toxin was detected from the CD NAP1/027 strain when grown in the presence of CFS extract from co-cultured selected strains diluted up to 1:10. When extract of NAP1/027 containing high amounts toxin A and toxin B was incubated with live LAB and bifidobacteria, toxicity was inhibited, indicating that selected strains of LAB and bifidobacteria exhibit anti-toxin activity. AMA of CFS produced by different combinations of LAB LU 28, LAB LU 33, Bif LU 10 and Bif LU 30 is ascribed not only to acids but also to heat stable extracellular antimicrobial proteins/peptides. A composition comprising the strains LAB LU 28, LAB LU 33, Bif LU 10 and Bif LU 30 showed AMA against hypervirulent CD strain NAP1/027, *S. aureus, Sal. typhimurim* and ESBL *E. coli* (Table 3 & Table 4).

Furthermore, the above selected probiotic strain combination was co-cultured with CD NAP1/027 in protease peptone yeast extract glucose with 0.05% (w/v) L-cysteine hydrochloride media (pH 7.2). CD NAP1/027 showed a 2 log cfu reduction in growth and the CD toxin A and toxin B productions were strongly inhibited after 24 h growth in comparison to CD grown alone in PYG. It can therefore be concluded that a composition including two or more of the strains LAB LU 28, LAB LU 33, Bif 10 and Bif 30 exhibits synergy leading to enhanced AMA against gut pathogens.

Co-feeding: Probiotics+Prebiotics

To develop a multi-strain probiotic or a synbiotic, it is important to select efficient strains with high prebiotic score and/or prebiotic index to restore gut microbiota with beneficial microbes in the subject's gut.

The initial screening included FOS, GOS, XOS; IMOS and Lactulose (Table 5). Also, other natural polysaccharides like resistant starch (RS) from wheat, gum arabic, beta glucan, xylan, pectin and inulin were evaluated for their prebiotic potential.

FOS is well known for its bifidogenic and lactogenic effect, but it may cause mucosal irritation in humans and enhance translocation of *Salmonella enterica* in antibiotic treated mice, a disadvantage that encouraged the inventors to screen GOS, IMOS, XOS and lactulose as prebiotic instead of FOS.

Most of the selected probiotic strains (Table 2) degraded more than one prebiotic component (Table 5). A prebiotic score (PS) was developed for each selected strain by determining the relative growth of each strain in an individual prebiotic compared to glucose.

TABLE 5

Prebiotic score for LAB and bifidobacteria

| Bacterial strain | GOS | FOS | XOS | IMOS | Lactulose | RS |
|---|---|---|---|---|---|---|
| LAB LU 33 | – | – | – | + | + | – |
| LAB LU 28 | 3+ | – | – | 3+ | 2+ | – |
| *L. rhamnosus* LMG 18243(LGG) | – | – | – | – | – | – |
| Bif LU 10 | 3+ | 2+ | – | 3+ | 3+ | 2+ |
| Bif LU 29 | 3+ | 3+ | 3+ | 3+ | 3+ | – |

TABLE 5-continued

Prebiotic score for LAB and bifidobacteria

| Bacterial strain | GOS | FOS | XOS | IMOS | Lactulose | RS |
|---|---|---|---|---|---|---|
| Bif LU 30 | 3+ | 3+ | 3+ | 3+ | 3+ | – |
| *B. lactis* JCM 10602 | 2+ | 2+ | 2+ | 2+ | 2+ | – |

Score definition:
–, No degradation (0 mm);
+, Weak (1 mm);
2+, Moderate (2 mm);
3+, Strong degradation (3 mm) &
ND, Not determined.

Co-culture of Mixed Probiotics with Different Combinations of Prebiotics

In the co-culture experiment above, it was shown that the selected strains were compatible with each other as they did not exhibit AMA against each other. The same selected strains were co-cultured in the presence of a single prebiotic, a combination of prebiotics and a combination of prebiotics with SS under pH uncontrolled conditions, to further investigate the possibility of synergism between the probiotic strains.

The strains LAB LU 28, LAB LU 33, BIF LU 10 and BIF LU 30 were mixed and sub-cultured on MRSC agar at 37° C. for 48 h. Single colonies were inoculated into 5 ml of a pre-reduced MRSC broth and sub-cultured thrice. Each culture was harvested, washed as above and re-suspended in PBS. The four selected probiotic strains were inoculated as a mix to get a final absorbance of 0.5 units (i.e. 0.125 per strain) in 5 ml of pre-reduced MRSC broth with 1% (w/v) (a) GOS, IMOS and soluble starch (SS) in a mixture (1:1:1), (b) IMOS and GOS (1:1), (c) GOS and SS (1:1), (d) GOS and (e) SS tubes were incubated under anaerobic condition for 24 h. Samples collected after 0, and 24 h and 100 microliters of culture broth was serially diluted and 50 microliters was spread on MRS agar (for LAB) and Bereens agar (for bifidobacteria), to determine the viable counts in terms of CFU/ml.

The total number of *Lactobacillus* and bifidobacteria on different combinations of single and mixed prebiotics are shown in Table 6. With glucose (GLU), GOS and IMOS/GOS, total bifidobacteria counts were higher than total LAB. With SS, increases in number of LAB and bifidobacteria were equal. With SS/GOS and SS/IMOS/GOS, total LAB counts were higher than bifidobacterial counts. The order of increase in log CFU/ml for LAB is SS/IMOS/GOS>SS/GOS>GOS>SS>IMOS/GOS>GLU and for bifidobacteria IMOS/GOS>GOS>GLU>SS/IMOS/GOS>SS>SS/GOS (Table 6).

TABLE 6

Total lactobacilli and total bifidobacteria during co-culture experiment after 0 and 24 h of growth.

| | 0 h (log CFU/ml) | | 24 h (log CFU/ml) | |
|---|---|---|---|---|
| Co-culture combination | Total LAB | Total bifidobacteria | Total LAB | Total bifidobacteria |
| GOS | 7.8 ± 0.1 | 7.4 ± 0.2 | 9.5 ± 0.3 | 9.6 ± 0.1 |
| SS | 7.6 ± 0.3 | 7.5 ± 0.5 | 8.9 ± 0.1 | 8.9 ± 0.2 |
| SS/GOS | 7.9 ± 0 | 7.8 ± 0.1 | 9.7 ± 0.2 | 9.7 ± 0.2 |
| IMOS/GOS | 7.2 ± 0.1 | 6.7 ± 0.3 | 8.9 ± 0 | 9 ± 0.1 |
| SS/IMOS/GOS | 7.5 ± 0.1 | 7.4 ± 0.2 | 9.5 ± 0.1 | 9.3 ± 0.2 |
| GLU | 7.6 ± 0.4 | 7.5 ± 0.3 | 8.6 ± 0.3 | 9.5 ± 0.1 |

Co-culture of LAB LU 33 and Bif LU 10 on Soluble Starch for Co-feeding

To elucidate a possible co-feeding and growth enhancement of the non-starch degrading strain LAB LU 33 with the starch degrading strain Bif LU 10, these strains were co-cultured in MRSC broth with 1% (w/v) of SS as sole carbon source. Co-culture of Bif LU 10 and LAB LU 33 enhanced the growth of LAB LU 33. The intermediate metabolites produced during the starch degradation supported the growth of LAB LU 33 (Table 7). Starch degradation is important to maintain a normal colonic environment, and enhance the growth of other beneficial microbes to restore gut microflora. The decrease in pH during the metabolism of starch didn't inhibit LAB LU 33, and both these strains are compatible with each other and show synergistic activity. The synergy exhibited by LAB 33 and Bif LU 10 surprisingly turned out to be strain-specific. When LAB LU 28, also a non-starch degrading strain, and Bif LU 10, were grown in the presence of RS, growth of LAB LU 28 was not stimulated. The same observation was made when the well-known probiotic strain *L. rhamnosus* GG, a non-starch degrading strain, was co-cultured with the starch-degrading strain Bif LU 10 in the presence of SS; *L. rhamnosus* GG growth was not stimulated. These two examples indicate that cross feeding is specific to selected strains used in combination with each other. Cross-feeding is apparently not an obvious property even among strains of the same genus.

TABLE 7

Co-feeding of non-starch degrading LAB
with starch degrading Bif LU 10 on SS

| Co-culture combination | Viability of LAB cells (log cfu/ml) | | |
|---|---|---|---|
| | 0 h | 24 h | 48 h |
| LAB LU 33 | 6.4 ± 0.07 | 7 ± 0.047 | 7.3 ± 0.012 |
| LAB LU 33 + Bif LU 10 | 6.3 ± 0.17 | 7.9 ± 0.06 | 8.2 ± 0.22 |
| LGG | 6.3 ± 0.14 | 7.5 ± 0.2 | 6.8 ± 0.2 |
| LGG + Bif LU 10 | 6.36 ± 0.14 | 7.4 ± 0.2 | 7 ± 0.2 |
| LAB LU 28 + Bif LU 10 | 7.9 ± 0 | 8.7 ± 0.3 | 8.3 ± 0.1 |

Net increase in log CFU of LAB in a co-culture is calculated using formula = (Log CFU at $T_{48h}$ – Log CFU at $T_{0h}$ of F8 with B 46+ soluble Starch) – (Log CFU at $T_{48h}$ – Log CFU at $T_{0h}$ of F8 in the presence of soluble starch).

AMA of Co-cultured Extract Against Human Pathogens

AMA of extracts from two or more of the selected strains (Table 2) co-cultured with different combinations of prebiotics was determined against gut pathogens. It was found that all CFS grown with different combination of prebiotics exhibited AMA against pathogens ESBL *E. coli*, *S. aureus*, *C. difficile* 2167 and NAP1/027 (Table 8). When the CFS of co-cultured extract was incubated with CD extract containing toxin, >70% of the toxic effect was inhibited, indicating that acids produced in the CFS exhibit antitoxin activity.

TABLE 8

AMA exhibited by the selected strains LAB LU 28,
LAB LU 33, Bif LU 10 and Bif LU 30 during co-culture
in different combinations of prebiotics.

| Prebiotic used in co-culture (dilution of CFS) | C. difficile CD 2167 | C. difficile CD 027 | S. aureus | ESBL E. coli |
|---|---|---|---|---|
| GLU (1:1) | 56 ± 2 | 54 ± 2 # | 89 ± 0.5 | 89 ± 0.1 |
| GLU (1:10) | — | 66 ± 3 # | 35 ± 5 | 9 ± 6 |
| GLU (1:100) | — | — | 4 ± 5 | 8 ± 1 |
| IMOS (1:1) | 65 ± 1 | 63 ± 3 # | 91 ± 1 | 91 ± 0.1 |
| IMOS (1:10) | 4 ± 2 | — | 30 ± 1 | 17 ± 8 |
| IMOS (1:100) | — | — | 4 ± 8 | — |
| GOS (1:1) | 49 ± 2 | 48 ± 2 # | 89 ± 0.2 | 88 ± 0.3 |
| GOS (1:10) | 44 ± 15 | 60 ± 3 # | 62 ± 2 | 18 ± 0.8 |
| IMOS/GOS (1:1) | 50 ± 1 | 51 ± 2 # | 90 ± 0.3 | 90 ± 0.4 |
| IMOS/GOS (1:10) | — | — | 39 ± 9 | 15 ± 4 |
| IMOS/GOS (1:100) | — | — | 61 ± 0.1 | — |
| SS/GOS (1:1) | 63 ± 1 | 61 ± 1 # | 89 ± 0.2 | 79 ± 15 |
| SS/GOS (1:10) | — | — | 7 ± 1 | 9 ± 8 |
| SS/IMOS/GOS (1:1) | 59 ± 2 | 61 ± 1 # | 89 ± 0.3 | 88 ± 0.5 |
| SS/IMOS/GOS (1:10) | — | 26 ± 17 | 17 ± 3 | — |

TABLE 8-continued

AMA exhibited by the selected strains LAB LU 28,
LAB LU 33, Bif LU 10 and Bif LU 30 during co-culture
in different combinations of prebiotics.

| Prebiotic used in co-culture (dilution of CFS) | C. difficile CD 2167 | C. difficile CD 027 | S. aureus | ESBL E. coli |
|---|---|---|---|---|
| SS/IMOS/GOS (1:100) | — | 6 ± 3 | — | — |
| RS/FOS/GOS/XOS (1:1) | 75 ± 0 | 73 | nd | nd |
| RS/FOS/GOS/XOS (1:10) | — | — | nd | nd |
| RS/Lactulose/IMOS/GOS (1:1) | 76 ± 0.3 | 72 ± 0 | nd | nd |
| RS/Lactulose/IMOS/GOS (1:10) | 78 ± 9 | 80 ± 0.3 | nd | nd |

— no inhibition, nd—not determined, CFS was obtained from MRS-BB containing 1% total prebiotics or glucose.
toxin level were not detected in these samples i.e. toxins were inhibited; toxin A and toxin B, virulence factor responsible for CD infection determined by ELISA assay It can be concluded that selected strains in the present composition possess high ability to degrade prebiotics. Co-culturing of the selected strains with different combinations of prebiotics gave different ratios of LAB/bif depending on the ability of strains to degrade prebiotics. Also it was found that metabolism by starch degrading strain Bif LU 10 stimulated the growth of non-starch degrading strain LAB LU 33. It should also be pointed out that the selected strains exhibited high AMA against gut pathogens, depending on the combination of different prebiotics utilized during culture (see Table 8.

Co-feeding: Pathogen+Prebiotics

As described above, *C. difficile*, ESBL *E. coli*, *S. aureus*, *S. typhimurium*, are human pathogens. Therefore it is essential to screen whether such pathogens are able to degrade and utilise the prebiotics present in the synbiotic mixture. Tests showed that none of the human pathogens; five clinical isolates of *C. difficile* including hypervirulent strain NAP1/027, *S. aureus*, ESBL *E. coli*, and *S. typhimurium* from LU Hospital were able to utilize FOS, GOS, IMOS, XOS, inulin, RS, SS, pectin or xylan. Hence, human pathogens did not exhibit prebiotic degrading ability which is very encouraging for the development of a cocktail of probiotics and prebiotics to combat gut infection.

Stress Pulsing and In vitro Gastro-intestinal-tract (GIT) Simulation for the Evaluation of Selected Strains A simple and reliable in vitro method was developed to simulate in vivo gastric transit conditions. This was done by exposing the selected probiotic strains to a combined acid (for 30 min), and bile stress pulse for 4 h to mimic in vivo gastrointestinal transit (GITS) at 37° C., aerobically (LAB) and anaerobically (bifidobacteria). First cells were subjected to acid stress in the MRSC/MRS medium at pH 2.5. After 30 min cells were washed with PBS and stressed with MRSC/MRS comprising porcine bile 5% (v/v) for 4 h. The viability of the strains was determined after 30 min and 4 h. MRSC broth without acid or bile stress was used as a control. To study prebiotic degrading ability of the stressed pulsed cells, they were also washed and inoculated into MRSC broth with different prebiotics or glucose. Unstressed cells were used as control.

Three strains, LAB LU 28, LAB LU 33 and LGG, showed 100% viability upon stress pulsing. BIF LU 30 and Bif LU 10 showed 100 and 40% viability respectively at the end of the bile phase in the GI transit model. The reference strain, *B. lactis* JCM 10602 (Bb12), showed 85% viability after GI transit. The order of robustness i.e. tolerance in a GI-like transit simulation is as follows: Bif LU 30>*B. lactis* JCM 10602>Bif LU 10.

Ideally in vivo, selected strains reach various parts of the gut in a viable form and multiply well using prebiotics as food in order to exert their probiotic functions. The ability of the strains in the probiotic mix to metabolize prebiotic supplements was analyzed in a GI-like transit, i.e. after stress pulsing. Stress pulsed and unstressed cells of LAB LU 28 showed a similar growth with GOS and glucose. Stress pulsed cells of Bif LU 10 showed longer lag phase, but after 24 h their growth pattern was similar to that of unstressed cells in the presence of IMOS, GOS and FOS. Moreover, growth of stressed pulsed Bif LU 10 was higher in GOS, IMOS, FOS compared to glucose. The Bif LU 30 strain showed the same growth kinetics as the unstressed cells when grown with GOS, XOS and glucose.

For a composition, the probiotic strains will be selected based on robustness (i.e. stress pulsing), AMA against *C. difficile* and other enteric pathogens, ability to use prebiotics, the ability to reach the intestine without losing their metabolic activity, the ability to multiply in the presence of prebiotics of a synbiotic mix and exert their probiotic effects.

CFS of LAB LU 28 and LAB LU 33 grown in the presence of 5% porcine bile retained more than 60% AMA against *S. aureus, S. typhimurium, C. difficile* 2167 and *C. difficile* NAP1/027. Bif LU 10 and Bif LU 30 grown in the presence of 5% porcine bile retained more than 60% AMA against *C. difficile* 2167 and *C. difficile* 027. Selected strains grown in the presence of 5% porcine bile retained AMA against *C. difficile* and other gastrointestinal pathogens (including *S. typhimurium*, ESBL *E. coli, S. aureus*).

Robust cells produced after stress pulsing will be useful to produce higher cell yield during freeze drying and final packing of synbiotic formulation with prebiotics and RS.

Use of a Gastro-intestinal-tract Simulator (GITS) to Evaluate Survival of Selected Probiotic Strains in Mixed Cultures.

The GITS consists of a 1 L "Biobundle" fermentor, a biocontroller ADI 1030 and balances, connected to the PC and is controlled by a cultivation program "BioXpert". Temperature, pH, culture volume, agitation, oxygen content and speed rates of liquids (i.e. HCl, $NaHCO_3$, bile salts, feeding medium) is controlled by the program. The GITS is a fermentor with several vessels (P1-P5) that simulates the gastrointestinal tract (FIG. 1).

A bacterial suspension is injected and stays in the first vessel which simulates the stomach (pH 3.0), for 3 h. The bacterial suspension is thereafter pumped into a second vessel simulating the small intestine with bile, pH 6.5, and the large intestine (dilution, pH 6.0).

At the start of simulation, 100 ml of 0.01M HCl was added into fermenter to simulate the empty stomach. Selected strains of multistrain probiotics (i) Bif LU 10, Bif LU 29, LAB LU 28 (ii) Bif LU 10, Bif LU 29, Bif LU 30, LAB LU 28 (iii) Bif LU 10, Bif LU 30, LAB LU 28, LAB LU 33 in 200 ml "model food" with medium containing tryptone yeast extract containing cysteine HCl with prebiotic mix: FOS, GOS, XOS was pumped into fermenter.

As shown in FIG. 1, P1, P2, P3, P4, and P5 show the key sampling points corresponding to beginning of the experiment (P1), gastric phase (P2), bile phase (P3); dilution phase to remove bile (P4) and at the end of the experiment (P5). The pH in the vessel was titrated to 3.0 by adding 1M HCl at a rate of 20 mmol $h^{-1}$ to simulate stomach conditions. After pH 3 was reached, the content of the bioreactor was adjusted to pH 6.0 by adding 1M $NaHCO_3$. Porcine bile (30 ml 30% solution) up to 3% was added to the fermenter and incubated for 30 min. The content was diluted until the total experiment for 24 h with a dilution medium containing tryptone yeast extract containing cysteine HCl with a prebiotic mix of FOS, GOS, XOS (3 g/L per perbiotic). Colony forming bacteria were enumerated as described above in the co-culture experiment during different phases of the simulation. REP-PCR fingerprinting analysis with $(GTG)_5$ primer was performed for 20-40 selected colonies from the beginning and end of experiments. Bacterial cells were quantified in terms of total DNA copy number using qPCR. The concentrations of organic acids (lactate, acetate, formate) and ethanol in the culture media were analyzed by liquid chromatography (Alliance 2795 system), using a BioRad HPX-87H column (Hercules, Calif.) with isocratic elution of 0.005 M $H_2SO_4$ at a flow rate of 0.6 mL $min^{-1}$ and at 35° C. Refractive index (RI) detector (model 2414; Waters Corp) was used for detection and quantification of the substances.

In a composition containing Bif LU 10, Bif LU 29, and LAB LU 28 and the prebiotic mix FOS, XOS or GOS, Bif LU 10 and LAB LU 28 strains survived well during the simulated GIT conditions (Table 9). A decrease of Bif LU 10 was more pronounced during acid and bile incubation and increased during the dilution phase. (The numbers of BIF LU 29 were significantly lower at the end of the experiment and that strain was not detected in the culture).

TABLE 9

Bacterial numbers ($log^{10}$ cfu $ml^{-1}$) as counted on MRS agar. Total number was enumerated on MRS-C agar anaerobically, LAB LU 28 on MRS agar aerobically.

| Time | TOTAL | LAB LU 28 | Bif LU 10 and Bif LU 29 |
|---|---|---|---|
| 0 | 8.69 | 8.60 | 8.04 |
| 00:30, pH 3 | 8.84 | 8.81 | ND |
| 00:40, bile 3% | 8.53 | 8.23 | ND |
| 01:13, bile 30 min | 8.30 | 8.30 | ND |
| 05:07 | 8.08 | 8.08 | ND |
| 18:06, dilution 17 h | 8.46 | 8.28 | 8.00 |
| 20:30 | 8.73 | 8.23 | 8.58 |
| 24:00, dilution 23 h | 8.68 | 8.11 | 8.57 |

ND—not determined

Production of lactate, acetate and ethanol in ratio 2:5:1 suggests better growth of bifidobacteria during the "large intestine" phase. However, lactobacilli can theoretically produce acetate also under glucose-limited conditions.

With a composition containing Bif LU 10, Bif LU 29, Bif LU 30, LAB LU 28 in equal amounts at the start of the experiment, the strain distribution was about 73% of LAB LU 28, 21% Bif LU 30 and 6% Bif LU 10 at the end of the GITS experiment. These results indicate good survival and growth of Bif LU 10, Bif LU 30 and LAB LU 28 in this combination. With a composition containing the strains LAB LU 28, LAB LU 33, Bif LU 10 and Bif LU 30 with a prebiotic mix containing FOS, XOS, GOS, no significant decrease in the numbers of LAB or bifidobacteria was detected at the end of the GITS experiment.

Figure 2:
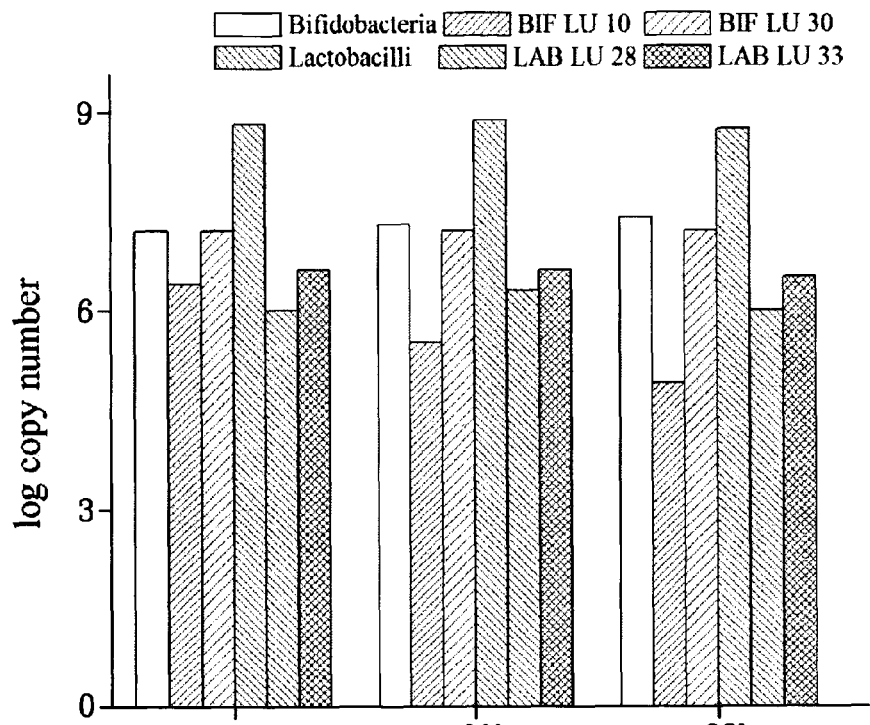
FIG. 2 Bacterial counts during Gastro Intestinal transit like simulation (GITS) as determined by qPCR.

Each biomass was analysed by qPCR for total DNA copy numbers of the LAB and bifidobacteria strains as well as the proportion of LAB LU 28, LAB LU 33, Bif LU 10 and Bif LU 30 (FIG. 2). Results showed that the log copy numbers of LAB LU 28, LAB LU 33, and Bif LU 30 remained the same after 20 h and at the end of the experiment.

LAB LU 28 and LAB LU 33 strains survived the acid and bile stress well and were able to grow with oligosaccharides as carbon source. The proportion of LAB LU 28 and LAB LU 33 compared to the other strains present in the mix increased significantly during the simulation, according to results of the rep-PCR.

Bif LU 10 and Bif LU 30 were detected at the end of experiment, although their proportion in the probiotic mix had decreased during the simulation. The Bif LU 29 is less tolerant to bile and the counts were always lower compared with the other strains at start of the experiment and were not detected at the end of the experiment.

At the start of the simulation, LAB colony counts were always higher compared with the Bif LU 10 and Bif LU 30, and LAB were able to multiply successfully during the dilution phase. The bifidobacteria recovered better from the acid/bile stress than LAB strains did, in spite of more severe initial decline during acid/bile treatments. This due to a preferred consumption of oligosaccharides compared with the LAB strains during the dilution phase. There is a good correlation between single strain studies as described in stress pulsing section below and co-cultures of these probiotic strains, confirming their robustness in the GI-like transit model.

It is noteworthy that in a GITS experiment performed with LAB LU 28, LAB LU 33, Bif LU 10, Bif LU 30 and *B. pseudocatenulatum* 1200 strains, wherein SS (5 g/L) and GOS (5 g/L) were used as major carbon sources, the LAB LU 33 strain was the strongest in this combination with SS/GOS despite the fact that this strain does not utilize SS or GOS.

The GITS experiment confirmed the new concept of cross feeding exhibited by Bif LU 10 and LAB LU 33 when grown in presence of SS and GOS. LAB LU 33 is not able to use either SS or GOS. However, when grown in the presence of other selected strains, especially the only starch degrading strain in the composition i.e. Bif LU 10 and SS/GOS, counts of LAB LU 33 increased. Furthermore the robustness of strains during the GIT transit was also seen. It can be concluded that a composition containing LAB LU 28, LAB LU 33, Bif LU 10 and Bif LU 30 probiotic mix is stable in the GI-like transit model in a single vessel GITS model.

In these experiments, strains were selected based on a high prebiotic score. All four selected strains were grown in the presence of prebiotics and starch to design a synergistic synbiotic mix. It was found that these strains in the synbiotic mix were compatible with each other and the ratio of LAB/bif increased or decreased depending on the prebiotic degrading ability of the strains (prebiotic score Table 5) as well as their exhibited AMA against human pathogens. Furthermore, the synergy between probiotics with prebiotics enhanced growth of the non-starch degrading probiotic strains in the presence of starch degrading probiotic strains. The selected strains are robust, can withstand GI like transit, can keep metabolic activity, and are able to metabolise prebiotics.

Prevention of Infection Using Mouse Model

Compositions of the present invention can advantageously be used to colonize the intestinal mucosa of a subject, (and in particular) to prevent and treat infections, ameliorate symptoms, and prevent relapse of antibiotic-associated diarrhea (AAD) and/or infections caused by gastrointestinal pathogens in a subject.

Figure 3:
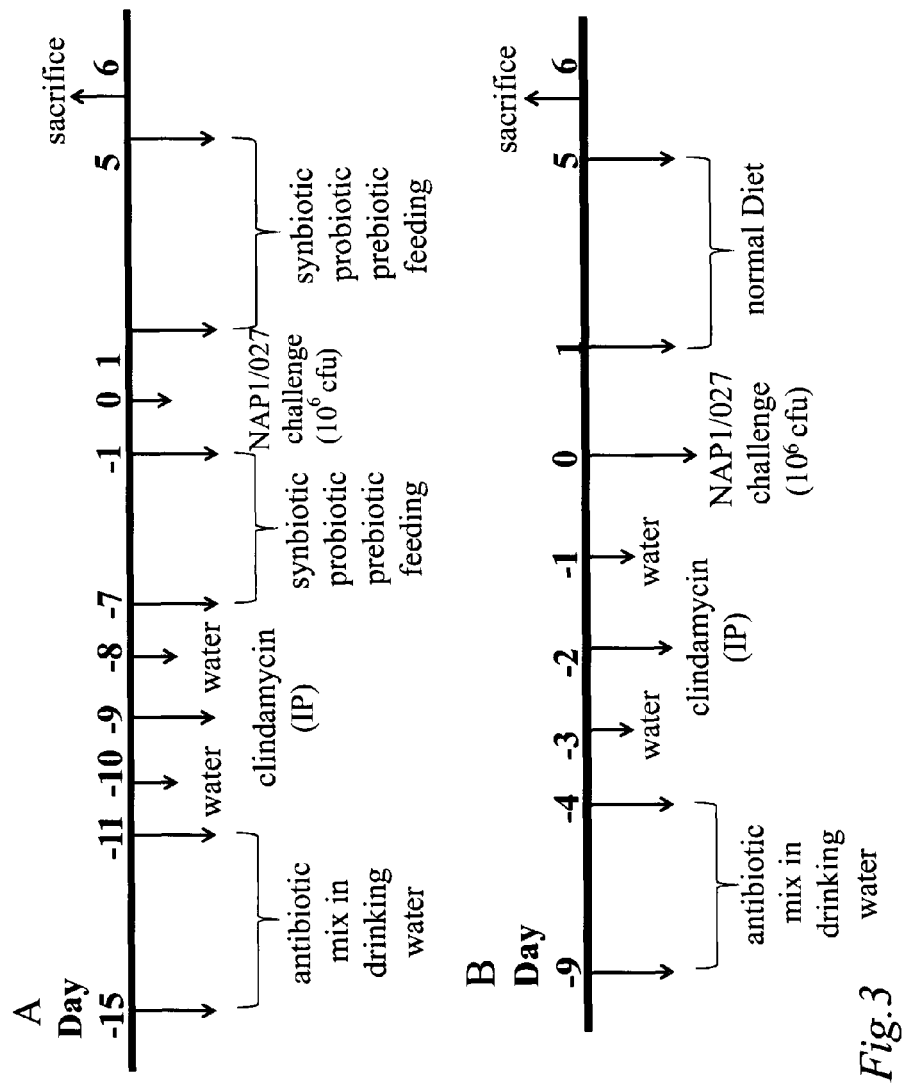
FIG. 3 Experimental design of the prevention of CDI in a murine model with a synbiotic, probiotic and prebiotic mix.

As described above, the selected strains (i.e. LAB LU 28, LAB LU 33, Bif LU 10 and Bif LU 30) all have high AMA against CD NAP1/027, are robust in terms of survival in GITS simulation, possesses ability to degrade at least one or more prebiotics used in the mix. To investigate the effect of the selected probiotic strains grown in the presence of the selected prebiotics, different combinations were tested in vivo using a mouse model. The detailed experimental schedule is shown in FIG. 3. Six to seven weeks old C57BL/6 mice were divided into four experimental groups. Group 1 (n=5) the synbiotic group was treated with "synbiotic mix" consisting of RS, IMOS, GOS and LAB LU 28, LAB LU 33, BIF LU 10 & BIF LU 30; Group 2 (n=6) the probiotic group, was treated with a "probiotic mix" consisting of LAB LU 28, LAB LU 33, BIF LU 10 & BIF LU 30; Group 3 (n=6) was treated with a "prebiotic mix" consisting of RS, IMOS, GOS; and Group 4 (n=7) comprised of "positive control" in which the animals were only infected with CD 027. Groups 1 and 2 were given a daily dose of $1\times10^{10}$ cfu/mouse of each probiotic strain.

The total prebiotic concentration was 5% (w/w) of the normal diet, calculated based on a 5 g daily feed consumption per mouse. RS was mixed with a low protein rodent diet (R70, Lantmännen, Malmö, Sweden) and pellets were prepared and fed daily. Group 4 (n=7) was a control group, infected with the NAP1/027 strain and did not receive any synbiotic, prebiotic or probiotic mixes. The indigenous mouse gut microflora was disrupted by giving an antibiotic mix for five days (days −15 to −11) diluted in the drinking water. An antibiotic cocktail of kanamycin, gentamicin, colistin, metronidazole, and vancomycin was prepared in drinking water and filter sterilized. On day nine (−9) all animals, including the control group, received a single dose of clindamycin (10 mg/kg) intraperitoneally. Groups 1-3 were fed with a synbiotic, probiotic and prebiotic mix for seven days (FIG. 3A). On day zero, all animals were challenged with $10^6$ cfu of NAP1/027 ($10^6$ cfu/mouse) by gastric tubing. The synbiotic, probiotic or prebiotic feeding of respective groups was further continued for another five days and on day six all animals were sacrificed by $CO_2$ asphyxia (FIG. 3A). Fresh caecal contents were collected aseptically for culture, real-time quantitative PCR (qPCR), histopathology and toxin tests. Antibiotic treatment of the control group (Group 4) was started in such a way that *C. difficile* infection (CDI) would fall at the same day as for Groups 1-3. This was done to maintain uniformity of CD dose used to infect the animals and to reduce experimental errors (FIG. 3B).

Figure 4:
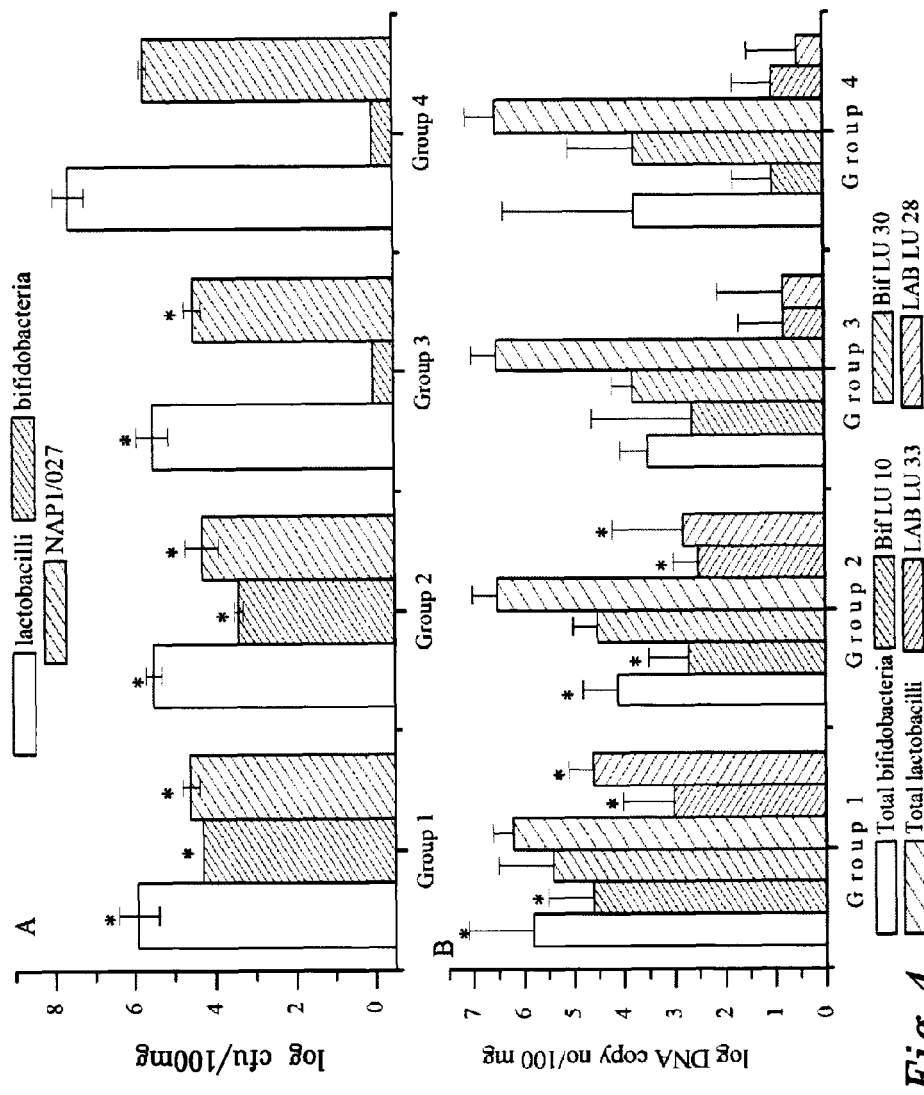
FIG. 4. Cecal count from pooled caecal contents of all animals within one group.

Total lactobacilli, bifidobacteria and NAP1/027 viable colony counts from pooled caecal contents of all animals within one group were analyzed (FIG. 4A). Colony counts of NAP1/027 were determined on Cefoxitin Fructose Fastidious plates under anaerobic conditions for 72 h at 37° C. Viable counts were expressed as log cfu/100 mg of caecal content. Furthermore, total DNA copy numbers as determined by qPCR of Bif LU 10, Bif LU 30, LAB LU 33 and LAB LU 28 in the caecal contents of the different animal groups. *P-value<0.05, was also determined (FIG. 4B).

It was found that feeding with a synbiotic composition comprising the four selected probiotic strains, with prebiotics IMOS, GOS and RS, prevented CDI compared to the control group where animals were severely sick because of colitis.

All animals in Groups 1-3 were healthy and no symptoms of diarrhea were observed. Three mice in Group 4 became severely sick after two days of CDI due to colitis and were therefore sacrified.

Colony counts of caeca contents in Groups 1-3 showed a significant reduction of NAP1/027 (P<0.05) compared with Group 4 animals. Lactobacilli colony counts were higher in Group 4 (P<0.05) compared with the other groups. Bifidobacteria colony counts were significantly higher in Groups 1 and 2 compared with Groups 3 and 4 (FIG. 4A). DNA log copy numbers of total bifidobacteria, Bif LU 10, LAB LU 28 and LAB LU 33 copy numbers were higher in Groups 1 and 2 compared with Groups 3 and 4 (P<0.05). The total lactobacilli log DNA copy numbers were similar in all four groups (FIG. 4B). In Group 1, the caeca content of 3/5 mice showed a moderate decline and two showed negative NAP1/027 DNA copy numbers. In Group 2, 1/6 mice showed a very low CD copy number and five were negative. In Group 3, 2/6 animals were negative, one showed very low CD DNA, two showed moderate and one showed very high NAP1/027 DNA copy numbers. In Group 4, the caeca content of four mice showed between 2-4 log copy numbers of NAP1/027 DNA.

Figure 5:
FIG. 5 Histopathology of cecal tissues of animals

FIG. 5 shows results from a histopathology investigation of cecum tissues obtained from the animals in the experiment. FIG. 5A shows the histopathology of cecum tissues of animals in Group 1 (synbiotic group), FIG. 5B; caeca of Group 2 (probiotic group) (40× view) reveals normal tubular glands and well preserved superficial columnar epithelium. FIG. 5C; caeca of Group 3 (prebiotic group) display small areas with irregular surface. Low numbers of polymorphs are visible between crypts in the lamina propria. FIG. 5D; caeca of Group 4 (control group) showing ulceration with effacement of mucosal epithelial cell lining and crypts in the cecum. The mucosa and sub-mucosa are hemorrhagic and show severe inflammatory edema.

Caecal samples of Groups 1-3 did not show any signs of inflammation but in Group 4, three animals were sacrificed due to a severe colitis (FIG. 5). The cecum of one animal in Group 1 and one in Group 3 showed scores 3+ and 2+ of inflammation. All of Group 2 animals showed no inflammation. All mice that showed inflammation of the cecum in Groups 1 and 4 were also positive for toxin A or B, in Group 2 all mice were toxin negative (Table 10).

TABLE 10 qPCR analyses of the NAP1/027 CD strain, histopathological scores and toxin values of the cecum contents of the four mice groups.

| Animal groups | Mouse no. | NAP1/027 DNA log copy number/100 mg | Histo-pathology[a] | Toxin values (RFV)[b] |
|---|---|---|---|---|
| Group 1 | 1 | 0 | 0 | neg |
| | 2 | 0 | 0 | eq |
| | 3 | 2 | 0 | neg |
| | 4 | 2 | +++ | pos (2.34) |
| | 5 | 4 | 0 | neg |
| Group 2 | 1 | 0 | 0 | neg |
| | 2 | 1 | 0 | neg |
| | 3 | 0 | 0 | neg |
| | 4 | 0 | 0 | neg |
| | 5 | 0 | 0 | neg |
| | 6 | 0 | 0 | neg |
| Group 3 | 1 | 5 | 0 | pos (4.14) |
| | 2 | 2 | 0 | neg |
| | 3 | 2 | 0 | neg |
| | 4 | 1 | 0 | neg |
| | 5 | 0 | 0 | neg |
| | 6 | 5 | ++ | eq |
| Group 4 | 1 | 4 | 0 | pos (6.09) |
| | 2 | 2 | 0 | pos (1.85) |
| | 3 | 3 | + | pos (1.77) |
| | 4 | 4 | ++++ | neg |
| | 5 | nd* | +++++ | nd |
| | 6 | Nd* | +++++ | nd |
| | 7 | Nd* | +++++ | nd |

[a]Histopathology scores: very severe: +++++, severe: ++++, moderate: +++, mild: ++, very mild: + significant lesions not observed.
[b]Relative fluorescence values. Cut-off levels for the toxin test: negative <0.13, equivocal >0.13 to 0.37, positive >0.37
*nd, not determined, animals were severely sick and killed due to infection. Caecal content could not be collected.

In conclusion, administration of a synbiotic mix containing four probiotic strains and GOS, IMOS and RS or a probiotic containing a multi-strain mix conferred a protective effect in the antibiotic treated mice against CDI with the NAP1/027 strain. Altogether, feeding with a synbiotic or a probiotic mixture protected the mice against CD infection, and a partial protection was provided by an equivalent prebiotic feeding. This is the first study on prevention of CDI in a mouse model using a novel concept of synbiotic and probiotic treatment. Restoration of Microbiota.

The effect of feeding a synbiotic supplement containing the probiotic strains LAB LU 28, LAB LU 30, Bif LU 10 and Bif LU 30 with the prebiotics GOS, IMOS and RS was investigated in a C57/BL/6 mouse model. Multiplication of probiotic mixes in faeces at different points after feeding and in the caecum at end of the experiment was followed.

Figure 6:
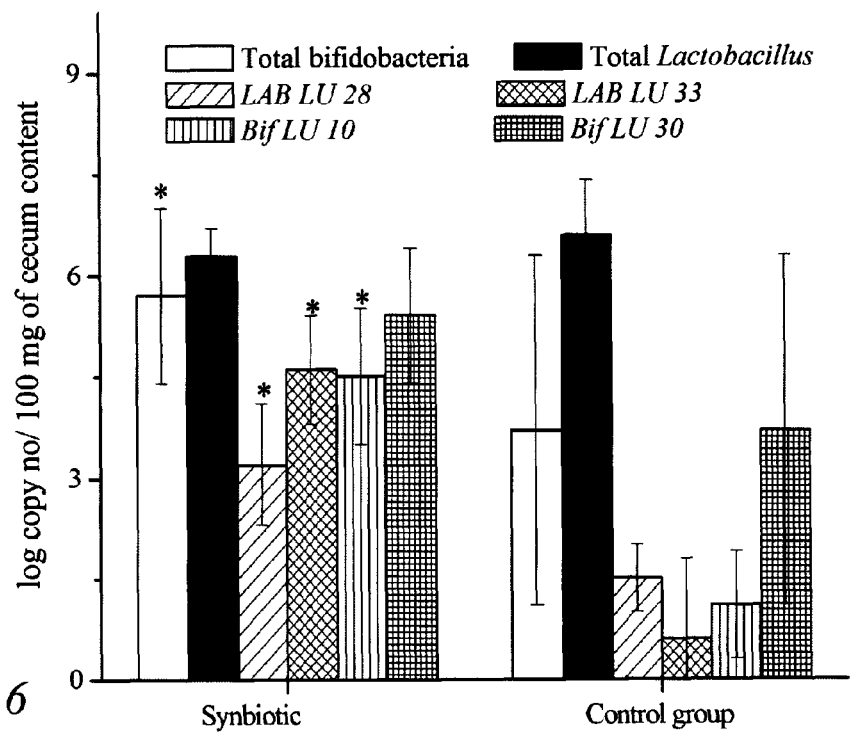
FIG. 6 qPCR results for caceal LAB and bifidobacteria in synbiotic group and control group.

Before feeding the probiotic mix in C57BL/6 mouse model, mice were treated with an antibiotic mix to disrupt the indigenous LAB and bifidobacteria microflora as described above in the prevention experiment. DNA copy numbers of total probiotic bifidobacteria, total lactobacilli, LAB LU 28, LAB LU 33, Bif LU 10 and Bif LU 30 in caecum of the synbiotic and control groups were determined by q PCR. Significance is expressed as * $P<0.05$ (FIG. 6).

In the synbiotic group, the total LAB and bifidobacteria increased after feeding the synbiotic mix to antibiotic treated mice in comparison to the control group. The total counts of caeca bifidobacteria were higher in the synbiotic group than in the control group and no cultivable bifidobacteria were detected. Total faecal bifidobacteria and Bif LU 10 counts increased during the middle of the synbiotic treatment, and at the end of the experiments. The DNA copies of feceal LAB LU 33, Bif LU 10 and Bif LU 30 were higher at the end of the experiment.

Caeca of the synbiotic group showed the highest bifidobacteria and LAB. LAB LU 28, LAB LU 33 and Bif LU 10 count compared to control group as determined by qPCR (FIG. 6). There was no significant difference in the LAB DNA copies between the synbiotic and control groups. DNA copy numbers of BIF LU 30 were higher in the symbiotic group compared to the control group, but no significant difference. Hence the probiotic strains multiplied well in the presence of prebiotics and RS in caecum of antibiotic treated mice, as total LAB and bifidobacteria counts increased significantly in faeces and caecum as determined by colony counts and qPCR. The fact that LAB LU 28, LAB LU 33, Bif LU 10 and Bif LU 30 were recovered from faecal and caecal samples, it can be concluded that utilization of prebiotics in a synbiotic mix, promoted multiplication and colonization of the selected probiotic strains in the murine gut. In the present composition of the four strains with GOS, IMOS and RS it was seen that the multiplication of each strain was in equal proportion in caecum.

Safety Experiment

The safety of the composition comprising LAB LU 28, LAB LU 33, Bif LU 10 and Bif LU 30 with GOS and RS was established in an immunocompromised C57/BL/6 mouse model. Mice were immunocompromised using methotrexate, an inhibitor of dihydrofolate reductase and DNA synthesis is widely used in cancer chemotherapy. Methotrexate (3.5 mg/Kg) was fed orally to mice for three days. After two days the synbiotic group were fed with $4 \times 10^{10}$ cfu/ml with 5% GOS in water. RS was mixed with feed and fed daily to mice for six days. On the $7^{th}$ day mice were killed and the liver, spleen, blood and kidney was collected for viability investigation using plate count method and liver for histopathology The results confirmed no translocation of bacteria to liver, blood, kidney, spleen and that histopathology of the liver was normal. Further it was found that the white blood cells counts were reduced in the control group after treatment with methotrexate, and that feeding the synbiotic supplement for 7 days raised the level of WBC count.

The invention claimed is:

1. A synbiotic composition comprising at least two bacterial strains selected from the group consisting of the *Lactobacillus* and *Bifidobacteria* genus, and one or more prebiotic substances, wherein:
    at least one of the bacterial strains is *Bifidobacterium breve* Bif LU 10 (deposit no: LMG P-26117) and capable of degrading starch; and
    at least one prebiotic substance is starch.

2. The synbiotic composition according to claim 1, wherein the starch is resistant starch (R8) and/or soluble starch (88).

3. The synbiotic composition according to claim 1, wherein one of said bacterial strains is a non-starch degrading strain.

4. The synbiotic composition according to claim 3, wherein the non-starch degrading bacterial strain is of the *Lactobacillus paracasei* species.

5. The synbiotic composition according to claim 3, wherein the non-starch degrading bacterial strain is LAB LU 33 (deposit no: LMG P-26118).

6. The synbiotic composition according to claim 1, further comprising one or more of the strains LAB LU 23 (deposit no: LMG-P-26119), LAB LU 28 (deposit no: LMG P-26120), BIF LU 29 (deposit no: LMG P-26115), and/or BIF LU 30 (deposit no: LMG P-26116).

7. The synbiotic composition according to claim 6, comprising at least LAB LU 33 (deposit no: LMG P-26118), and BIF LU 30 (deposit no: LMG P-26116).

8. The synbiotic composition according to claim 6, comprising at least LAB LU 33 (deposit no: LMG P-26118), BIF LU 30 (deposit no: LMG P-26116), and LAB LU 28 (deposit no: LMG P-26120).

9. The synbiotic composition according to claim 1, wherein one or more of the bacterial strains has been exposed to acid, bile and/or mucin during their production.

10. The synbiotic composition according to claim 1, further comprising a prebiotic substance of the group consisting of disaccharides, oligosaccharides, and/or polysaccharides.

11. A synbiotic composition according to claim 1, for use in the colonization of the intestinal mucosa of a subject.

12. A synbiotic composition according to claim 1, for use in the prevention, treatment of, amelioration of symptoms, and/or prevention of relapse of antibiotic-associated diarrhea (AAD) and/or infections caused by gastrointestinal pathogens in a subject.

13. The synbiotic composition for use according to claim 12, wherein the antibiotic-associated diarrhea (AAD) is induced by Clostridium difficile.

14. The synbiotic composition for use according to claim 12, wherein the infection by gastrointestinal pathogens is caused by *Salmonella, Campylobacter jejuni*, Extended Spectrum Beta Lactamase producing (ESBL) *E. coli*.

15. The synbiotic composition for use according to claim 11, wherein the subject is a mammal.

16. A method for the colonization of the intestinal mucosa of a subject, said method comprising the step of administering a synbiotic composition in an effective dose to a subject in need thereof, said synbiotic composition comprising a least two bacterial strains selected from the group consisting of the *Lactobacillus* and *Bifidobacteria genus*, and one or more prebiotic substances, wherein at least one of the bacterial strains is *Bifidobacterium breve* Bif LU 10 (deposit no: LMG P-26117) and capable of degrading starch; and at least one prebiotic substance is starch.

17. A method for treating a subject for antibiotic-associated diarrhea (AAD) and/or infections caused by gastrointestinal pathogens, said method comprising the step of administering a synbiotic composition in an effective dose to a subject in need thereof, said synbiotic composition comprising a least two bacterial strains selected from the group consisting of the *Lactobacillus* and *Bifidobacteria genus*, and one or more prebiotic substances, wherein at least one of the bacterial strains is *Bifidobacterium breve* Bif LU 10 (deposit no: LMG P-26117) and capable of degrading starch; and at least one prebiotic substance is starch.

* * * * *